US008612251B2

(12) United States Patent
Yourist et al.

(10) Patent No.: US 8,612,251 B2
(45) Date of Patent: Dec. 17, 2013

(54) COORDINATED HEALTH AND HUMAN SERVICES DELIVERY SYSTEM AND PROCESS

(75) Inventors: Jay E. Yourist, Miami, FL (US); Karl Joseph Krieger, Tallahassee, FL (US); Robert L. Dilworth, Gum Spring, VA (US); Zuhair Latif, Vernon Hills, IL (US); Louay Chaar, Miami, FL (US)

(73) Assignee: The Trinity Management Group, LLC, Miami, FL (US)

( * ) Notice: Subject to any disclaimer, the term of this patent is extended or adjusted under 35 U.S.C. 154(b) by 0 days.

(21) Appl. No.: 13/345,491

(22) Filed: Jan. 6, 2012

(65) Prior Publication Data

US 2012/0197659 A1 Aug. 2, 2012

Related U.S. Application Data

(63) Continuation of application No. 11/359,130, filed on Feb. 22, 2006, now abandoned.

(60) Provisional application No. 60/654,932, filed on Feb. 23, 2005.

(51) Int. Cl.
*G06Q 10/00* (2012.01)

(52) U.S. Cl.
USPC .................................................. 705/2; 705/3

(58) Field of Classification Search
USPC ............................................................. 705/2
See application file for complete search history.

(56) References Cited

PUBLICATIONS

Anthony Lehman et al., Intensive inpatient treatment of young adult chronic patients, Psychiatric Quarterly, vol. 58(3), p. 167-179, Fall 1986-1987, http://www.*
Drake et al., A Randomized clinical trial od supported employment for inner-city patients with severe mental disorders, Archives gen Psychiatry, 1999; 56:627-633, http://archpsyc.ama-assn.org/cgi/content/full/56/7/627.*
Hector W.H. Tsang, Ph.D., Social skills training to help mentally ill persons find and keep a job, psychiatric services, Jul. 2001 vol. 52 No. 7.*

* cited by examiner

*Primary Examiner* — Hiep V Nguyen
(74) *Attorney, Agent, or Firm* — Sheridan Ross PC

(57) ABSTRACT

A system (200) and method (500) is provided for a coordinated health care service delivery program. The method can include providing services to clients at high risk for chronic disease including co-morbidities and consequent disabilities associated with the chronic disease, linking community and vocational services (130) for facilitating community inclusion to supplement fundamental clinical and economic goals, creating a comprehensive and dynamic individual development plan (222) to involve the client and family members as active program team members for stressing client-centric collaborative goal setting, and applying action learning (226) to promote behavior modification and lifestyle change.

22 Claims, 12 Drawing Sheets

FIG 11
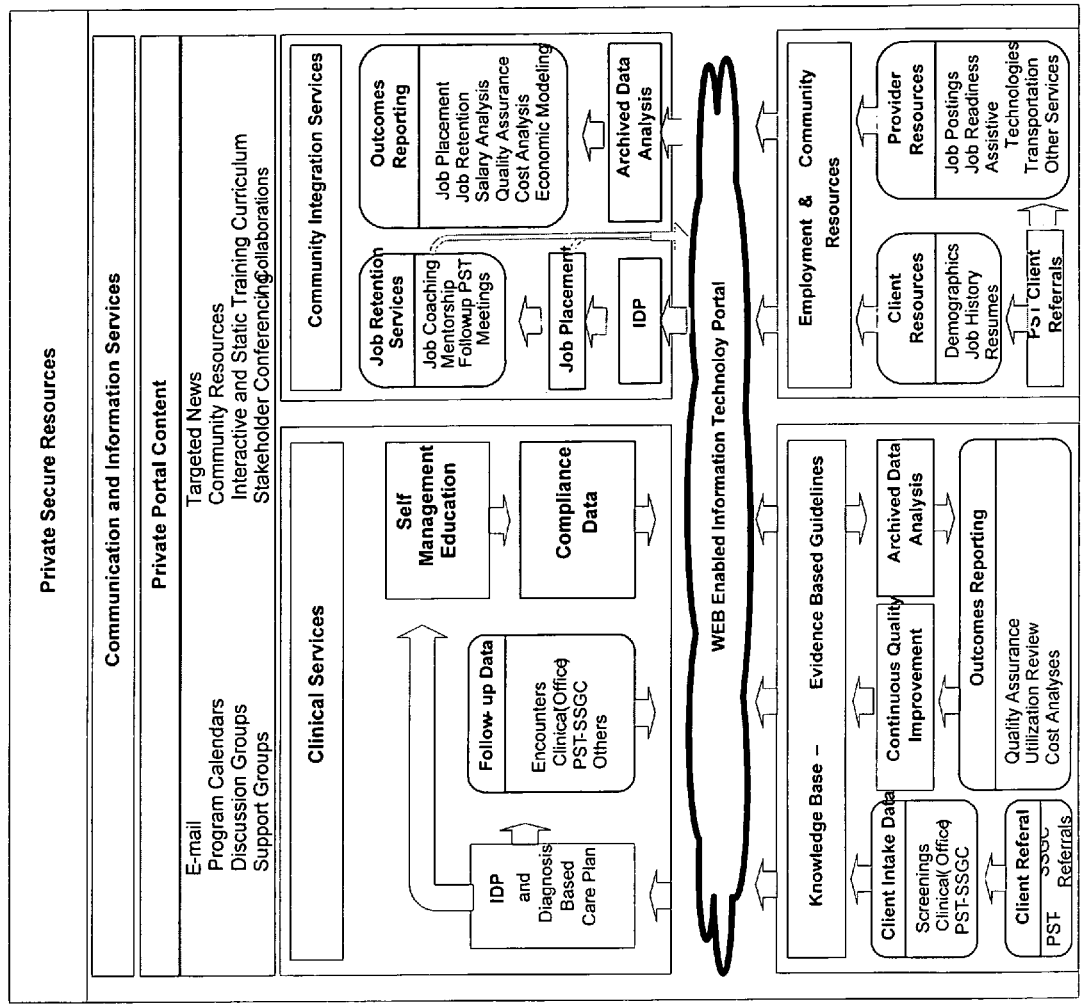
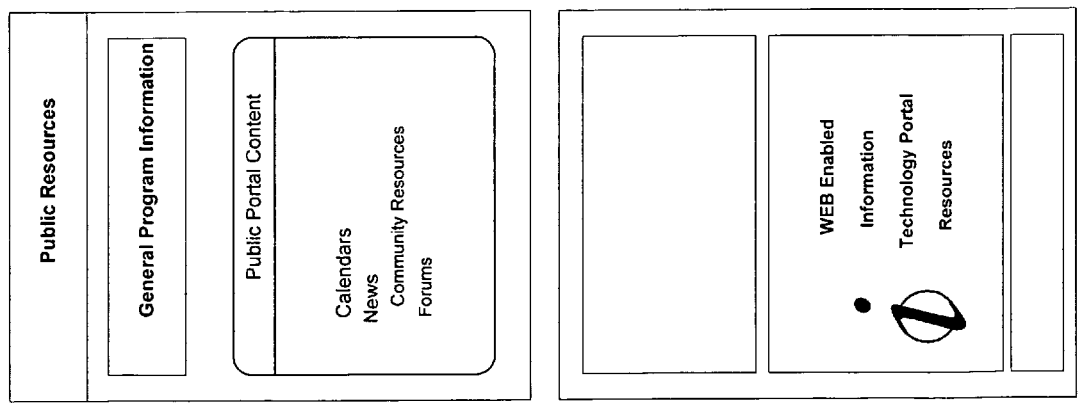

COORDINATED HEALTH AND HUMAN SERVICES DELIVERY SYSTEM AND PROCESS

CROSS REFERENCE TO RELATED APPLICATION

This application claims benefit of U.S. Provisional Application No. 60/654,932, filed Feb. 23, 2005, entitled "Coordinated Health and Human Services Management Network", by Jay E. Yourist, Karl J. Krieger, Robert L. Dilworth, and Zuhair Latif, which is hereby incorporated by reference.

FIELD OF THE INVENTION

The embodiments of the invention herein relate to management systems, and more particularly a method of health and human services delivery.

DESCRIPTION OF THE RELATED ART

The management practices of the healthcare system evolved in response to the high incidences of acute illnesses. However, over the last fifty years the prevalence of chronic illness has risen significantly. Chronic disease is a leading cause of disability and consequently unemployment for special needs populations including the elderly and disabled. Indirect non-clinical care costs frequently associated with disability, dependency, and joblessness are higher than the direct clinical care costs. Chronic disease is a leading cause of disability and unemployment undermining worker productivity and employability. Persons with chronic conditions may be less likely to work and may be more likely to have lower incomes. Minority populations have also demonstrated a higher incidence of chronic conditions, primarily diabetes and ensuing disability, further disenfranchising those particular populations.

Historically, healthcare practices were not coordinated but episodic and fragmented thereby proving to be increasingly inefficient for treating individuals of chronic diseases. In addition, service providers did not readily have access to client information which resulted in limited service delivery and cost inefficiency. Healthcare expenditures have steadily increased due to unnecessary hospital admissions, expensive and indecisive technologies, and the accumulation of conflicting clinical data. These expenditures have not provided substantive improvements in health status, community integration, or independent living.

Over the last twenty five years, policies and programs have been enacted to integrate services in order to promote cost efficiency and improve the quality of health care for such plans. Notably, the US Congress, through the Rehabilitation Act of 1973 and the IDEA Act of 1988, developed a policy to deliver a comprehensive plan to provide coordinated services to both adults and children with disabilities. Attempts to integrate or coordinate all or a part of the necessary services to achieve coordinated health care services have formerly included Disease and Care Management Programs, Workers Compensations Programs, Vocational Rehabilitation (Rehabilitation Act of 1973), IDEA Act of 1988, Ticket to Work Program, Comprehensive Elder Programs (PACE), Social HMOs, California Medi-Cal model for persons with disabilities (CHAT), Community Health Information Network (CHIN), and Integrated Healthcare Management (IHM).

The Ticket to Work Program; the Medicaid Buy-In; Benefits Planning, Assistance and Outreach (BPAO); and Protection and Advocacy for Beneficiaries of Social Security (PABSS) were all key initiatives contained in the Ticket to Work and Work Incentives Improvement Act of 1999 (TWWIIA) for increasing employment outcomes for beneficiaries. The goal of the Ticket Program was to give disability beneficiaries the opportunity to achieve long-term employment by providing them greater choices and Confidential (Social Security Administration) SSA Contract Proposal opportunities for employment. The legislation also removed barriers that previously influenced individual's choices between healthcare coverage and work. However, despite significant efforts by the SSA to provide employment opportunities such as the "Ticket to Work Program", less than 1% of all disability program beneficiaries return to gainful employment. (Wehman, 2003 a)

Considerable evidence and testimony from beneficiaries, advocates and providers have noted significant weaknesses in the Ticket to Work Program namely; 1) eligibility criteria exclude certain beneficiaries with significant return to work potential, 2) conflicts exist between the vocational rehabilitation system and the Ticket Program, and 3) the provider payment system has failed to recruit sufficient providers to guarantee beneficiary choice in job training and supports. Few beneficiaries and even fewer providers are participating in the Ticket program. The national statistics for Ticket assignments as of Sep. 27, 2005 indicate that 11,038,798 Tickets were issued and 104,537 tickets (0.95%) were assigned which is less than 1% of the total ticket distribution. Of those assigned Tickets 96,358 were assigned to Vocational Rehabilitation agencies (92.2%) and 8,179 to Employer Networks (ENs) (7.8%). These statistics mirror with those ticket assignment statistics in the State of Florida.

For example, in the State of Florida as of Sep. 27, 2005 out of 678,489 eligible ticket holders, only 5,688 Tickets were assigned (0.84%). Of the assigned tickets, 578 tickets were assigned to ENs (10%) and 5,110 Tickets were assigned to Florida's Division of Vocational Rehabilitation (90%). These numbers parallel national statistics where, nearly ninety percent of the current participants of the Ticket Program have been assigned to VR agencies. Consequently, overwhelming use of State VR agencies and the low numbers of ENs assisting current "Ticket" holders indicate that the goals of the Ticket Program to enhance access to services, primarily employment, are not being met. Studies have shown that beneficiaries would prefer to be employed if their primary benefits could remain intact, especially healthcare.

The Social Security Administration supports two disability programs: Social Security Disability Insurance (SSDI) and Supplemental Security Income (SSI). The programs consume approximately five percent of the federal budget, and are projected to become much more costly through 2012. The Ticket to Work and Work Incentives Improvement Act of 1999 was enacted to provide employment opportunities for beneficiaries, potentially reversing the growing claimant burden on the Social Security Administration. This has met with limited success and the suggested reforms and barrier removal strategies to improve the delivery of the Ticket Program tend to focus on policy changes and administrative systems in isolation, rather than following a holistic, integrative or a total systems approach. As the "baby boomer" population reaches the age where they are more susceptible to disability, critical economic issues impacting employment and rising health insurance costs can be expected to accelerate growth of these Social Security disability programs.

It has been verified that educating participants to make positive lifestyle choices can significantly reduce the complications attributed to chronic disease and disability. However, the traditional health care programs have been fragmented and ineffective. The policies and programs were mainly aimed at integrating primary and specialty healthcare services. They were not successful due in large part to the practical inability to access and share medical data. A major barrier to providing such services was also conflicting business interests, namely the reluctance for multiple healthcare providers to cooperate and coordinate their services due to increased competition. In addition, individual health and economic prosperity have typically been managed independently and in isolation with regard to the overall management of healthcare, wellness, community and vocational service delivery. The dissociation has compounded the problem to the detriment of both healthcare and economic remedies.

A need therefore exists for integrating and coordinating healthcare wellness, disease prevention, social, and employment service functions into a health care program to improve the quality of life for special needs populations such as elderly populations, minority populations, uninsured and underinsured populations, and persons with disabilities including those having chronic illness. Such a program can prepare a participant for employment, independence, and improved quality of life. In particular, a need also exists to establish a system to promote gainful employment for SSDI/SSI beneficiaries by providing a multi-disciplinary support system of services that promotes long term behavior modification, self-determination and systems change.

OBJECT OF THE INVENTION

An object of the invention is to bring together an array of interlocking modalities and constructs in ways that are mutually reinforcing and a part of one single overarching system. Typically, individual health care system components, such as peer support teams and circles, are usually used in isolation from one another rather than in juxtaposition with other systems or components of systems. In other cases there is no known existing parallel to these system pieces; that is, the manner in which principles of action learning are to be employed. The system component involved within the context of the invention, even if similar to systems that are already available in some form in the market place, have been specifically tailored to fit within the overall coordinated human and health services and delivery system to promote synergy. A core essence of the embodiments of the invention, as well as the uniqueness, is in its broad integration of essential services as a single system. The system is designed to holistically provide the necessary support mechanisms and services to not only improve the health status of those with chronic disease and disabilities of clients, but also to improve their quality of life, build their self-efficacy and level of self-confidence, and position clients for reentry into the workforce.

Referring to FIG. 1, an illustration for a connectivity of services is shown. The illustration represents the services as pieces of a puzzle connected together by an information technology (IT) platform. The IT platform is just one embodiment demonstrating how various system pieces can be widely integrated from a process standpoint, in support of chronic disease management, social services and support for those with chronic disease and/or disabilities. Various embodiments of the invention, in addition to the IT embodiment, are herein contemplated. The IT component can be considered as a tool to facilitate service coordination and data collection and analysis for a continuum of available services. Understandably, information technology can be interwoven throughout the services and delivery system in ways that optimize the sharing of critical information, both within the specific system and with external organizations, such as Vocational Rehabilitation. As a result, a coordinated human and health services and delivery program can be established wherein case management under such a program can become much more efficient. Rather than a series of individual and isolated system components or services, the framework creates an open system for coordination of services from the standpoint of information sharing across agency and organizational lines.

The business methods underlying the system of coordinated health and human service delivery herein presented can be applied to various contexts and operations. For example, the system can be configured to target Social Security Disability Insurance (SSDI) or Social Security Insurance (SSI) beneficiaries. Understandably, these beneficiaries are unique and require a broad range of support services to sustain community integrations which the coordinated health and human service delivery of the invention is uniquely adapted to provide. The coordinated health and human service delivery herein presented is flexible and adaptable to such unique demands. In one particular example, Federal and State systems have been minimally successful in enticing such individuals to actively return to the workplace (i.e., The Ticket-To-Work program). Consequently, one aspect of the invention is configurable for addressing the complexity of this problem. The embodiment of the invention can prove highly effective in providing coordinated services to other clientele groups as well. For instance, in one aspect, the underlying business methods can be readily customized to serve the elderly or to operate in different cultures in the United states or elsewhere. The system can evolve and adapt over time due to the inherent system flexibility afforded by the uniqueness and novelty of the coordinated delivery services model.

In certain aspects, the business methods underlying the system of coordinated health and human service delivery can be considered multi-disciplinary; that is, a holistic support system, which facilitates the linkage and efficient management of integrating clinical, community and vocational services. Accordingly, the system as a whole creates a seamless continuum of one coordinated service infrastructure. Notably, the execution of healthcare and social services in existence today is highly fragmented and not coordinated. The independent service modules are themselves not unique, but the architecture and deployment of this invention provides a coordinated system of essential services that represents a unique and novel systems approach.

The purposeful departure from independent service delivery is a hallmark feature of this invention. The underlying business methods of the invention provide an innovative approach that represents a paradigm shift in traditional case management and service delivery for primary care, specifically aimed at chronic disease and disability management. In one aspect, the invention is an evidence-based, population-based model that delivers culturally-relevant services customized for any population demographic, but is especially applicable for minority, underserved and underinsured communities with particular chronic diseases and/or disabilities. Uniquely designed, it employs action learning principles and peer support teams which foster individual responsibility and self-management under the auspices of support services mechanism and network, with the oversight of an advisory body of stakeholders. In one embodiment, the effective integration of these otherwise disparate services is realized through a proprietary IT platform.

In one aspect, for purposes of practical illustration, the method of coordinated services provided by the invention can promote gainful employment for SSDI/SSI beneficiaries through the deployment of a primary care and social delivery system in an underdeveloped country. It should be understood that the underlying business methods supporting the coordinated network of human and health services delivery may be applied to a variety of populations, particularly underserved communities, in need of coordination and/or consolidation of services.

Thus, in one aspect, the invention can provide a coordinated services support network to promote coordinated human and health services delivery for participant beneficiaries by providing a multi-disciplinary support system of services that promotes long term behavior modification, self-determination and systems change. This can include, but is not limited to, A. Developing a logistics infrastructure and training staff to provide essential services.
B. Partnering with Disability Vocational Resource (DVR) providers as a collaborator in most aspects of program from participant recruitment, plan development to data capture, analysis and evaluation.
C. Partnering with local and state agencies, to provide: 1) change management training; 2) appropriate program "cross training", and 3) information capture, sharing and analysis.
D. Recruiting and establishing a stakeholder provider network; Confidential SSA Contract Proposal.
E. Instituting a proactive recruitment strategy to enroll qualified SSDI/SSI beneficiary candidates.
F. Customizing self-management content targeting the broad needs of program participants in the areas of vocational, job readiness training, and health and fitness;
G. Articulating document and track Individual Development Plans (IDP) to capture personal and program goals for each participant, focusing on empowerment, self determination and employment goals.
H. Providing a secure IT platform to facilitate timely communication between program stakeholders and a virtual service coordination tool.
I. Designing and building a HIPPA compliant database to capture, archive, disseminate and analyze health, job readiness, economic and quality of life data.

SUMMARY

A health care delivery system and program is provided that coordinates human and health services to enhance gainful employment through individual development and principles of Action Learning. The coordinated human and health delivery system fosters self determination through "peer support" teams and multidisciplinary private/public partnerships which promote the capacity, quality and improved sustainability of healthcare, community service and meaningful employment opportunities.

In one aspect, embodiments of the invention concern a business method for coordinated health care services and delivery. The method can include providing services to clients at high risk for chronic disease including co-morbidities and consequent disabilities associated with the chronic disease, linking community and vocational services for facilitating community inclusion to supplement fundamental clinical and economic goals, creating a comprehensive and dynamic individual development plan to involve the client and family members as active program team members for stressing client-centric collaborative goal setting, and applying action learning to promote behavior modification and lifestyle change. Notably, the creation of the integrated development plan and the coordination of services is a fundamental feature to the inventive method of doing business.

The method can further include focusing on reach-out goals of the client's improved quality of life by encompassing clinical, social, and vocational measures and outcomes. This can include integrating a comprehensive set of healthcare, vocational, community integration and education services, coordinating and maintaining connectivity of the services while providing overall communication among program stakeholders, and providing tools and suitable media for customized data collection, capture, analysis, archiving, communication and information sharing. Notably, the development of an Individual Development Plan (IDP) in combination with self management education can promote personal accountability. Accordingly, utilization of action learning and peer support team principles can promote a client's self determination, advocacy, gainful employment and independence. The action learning can empower clients to solve problems with peers and case managers, wherein the problems may be associated with a clients' health management service and reimbursement policies.

In one aspect, the method can further include measuring and analyzing outcomes, and validating premises based on outcome indicators and metrics. Monitoring the implementation and coordination of the services with the care plan can provide continuous quality improvement. In one aspect, the data analysis results of the services can be combined with the individual development plan for developing new cost/economic models. In addition, evaluative mechanisms can be imposed for streamlining accountability of the coordinated health care services and delivery program. The evaluative mechanisms can include efficacy of recruitment, attainment of IDP goals, clinical goals outcome, job readiness and actual placements, assessment of participant satisfaction, and quality of life measures.

The method can further include providing a coordinated management architecture that places peer support teams at the core of a service delivery model. The model can rely upon personal relationships, trust factors, and emotional support established by peer-to-peer counseling. The peer support system can empower the client through customized self management education and problem solving skills for improving the client's health, community integration, employment readiness, financial well being, and overall quality of life.

In one arrangement, the coordinated health care delivery and services can be developed and implemented in phases consisting of primary and secondary intervention strategies. For example, a Primary interventions can be based on an individual development plan that focuses on an individual beneficiary. The secondary intervention can be system-based including clinical, educational, community, vocational services and benefit counseling.

Embodiments of the invention also concern a comprehensive service delivery program for coordinated health and human services management. In one aspect, the service delivery program can facilitate healthcare, community and vocational services for both Social Security Disability Insurance (SSDI) and Supplemental Security Income (SSI) beneficiaries, primarily those with disabilities related to chronic disease. The integrated approach can be critical for facilitating and sustaining gainful employment. It can provide a comprehensive set of essential coordinated supports, including healthcare. In practice, the delivery model can provide a confidential program of comprehensive and culturally sensitive coordinated services and lifestyle reform initiatives to achieve successful outcomes, specifically overall improved quality of life for persons with chronic disease and disabilities. The proposed program can target disability beneficiaries with, or at-risk for, chronic disease and disabilities.

The delivery program can provide services and products to manage participant problems in a useful, timely, efficient, cost-effective and participant-centric manner. Hospital staff members, healthcare providers and representatives of the pharmaceutical and medical device/research and development industry, and the participant among many other stakeholders, can be included within the delivery model to play important decision-making roles in determining and implementing the care plan for the participant's chronic illness. In one implementation, the program can target Ticket to Work assignees to Vocational Rehabilitation. The implementation can provide gainful employment opportunities and independent living, improved client-provider interactions through accessible and coordinated support services, lifestyle changes/behavior modification through self-management education and peer supported interactive problem solving, client empowerment and self-determination, and improved quality of life outcomes.

The delivery program can include an Individual Development Plan (IDP) that beneficiaries develop in conjunction with family members and other program stakeholders. The IDP can be a dynamic, personal template that articulates the beneficiary's goals, and which can be facilitated by "Peer Support Teams" to promote behavioral and lifestyle change using principles of Action Learning and interactive dialogue. The model can represent a paradigm change in traditional case management that can be a consumer-driven approach to provide support service coordination promoting self-determination and self-advocacy. Through this Systems Approach, Action Learning-based peer support, together with broad information sharing and analysis via an IT platform can facilitate the goals of Ticket to Work legislation.

The delivery program can include an intake assessment and recruitment module for population stratification and recruitment of clients having chronic disease or disability, a primary intervention module for developing an individual development plan and for enacting action-learning through peer support team intervention, a secondary intervention module for providing coordination of services through an IT platform, an information archive to coordinate services for monitoring and tracking client progress, a delivery process module for placing a client in a supportive, nurturing and learning environment for gaining access to the aforementioned services, and an evaluation module to analyze and measure the effectiveness of the coordinated service delivery system with regard to the level of community integration and re-employment of the client.

Embodiments of the invention also concern a program for coordinated health and human services delivery through an IT platform. The program can include assessing and recruiting clients, developing a team of professionals and third party providers, developing an individual development plan for the clients, supporting service groups and managing services for clients through action-learning and peer support team intervention, sharing and archiving information using an IT platform to consolidate data from the services and for monitoring and tracking client progress, delivering the services through the IT platform for providing on-line access to a multi-disciplinary team of experts, and analyzing and measuring the effectiveness of the coordinated service delivery program to provide healthcare, community integration, and employment service performance to the client.

Embodiments of the invention concern an information technology (IT) platform for providing coordinated health care and human services management. The platform can include a healthcare management service, a self-management service, a community and vocational service, and an outcomes research service. The IT platform can be a population-based, client-centric entity that combines access to self-management programs with a comprehensive continuum of services to facilitate a clients' functional and psychosocial needs for focusing the client on community integration and re-employment.

BRIEF DESCRIPTION OF THE DRAWINGS

The features of the system, which are believed to be novel, are set forth with particularity in the appended claims. The embodiments herein, can be understood by reference to the following description, taken in conjunction with the accompanying drawings, in the several figures of which like reference numerals identify like elements, and in which:

FIG. 11 illustrates an outcome report in accordance with an embodiment of the inventive arrangements.

GLOSSARY OF TERMS

Figure 1:
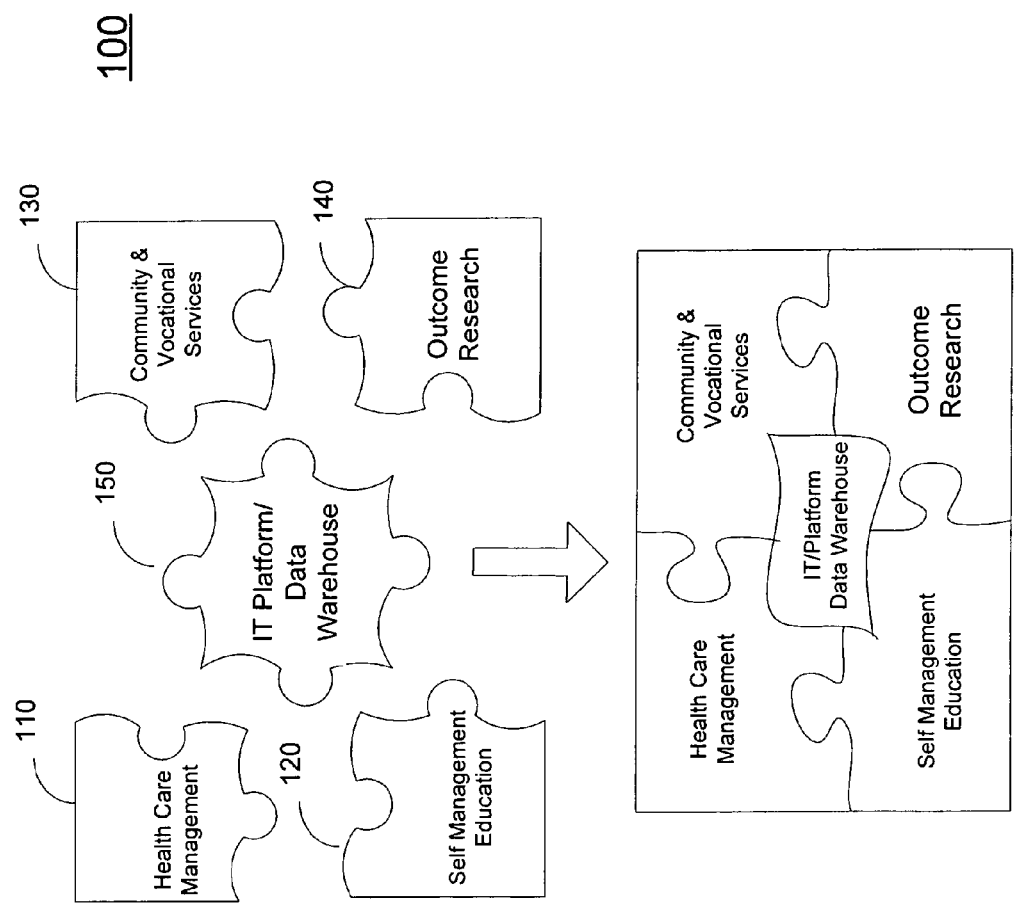
FIG. 1 depicts an information technology (IT) platform in accordance with an embodiment of the inventive arrangements.

A. Action Learning—Action Learning can be a process of reflecting on one's work and beliefs in an interactive and supportive environment of one's peers for the purpose of gaining new insights and resolving real business, personal or community problems in real time (expression of self determination).

B. Advisory Council—A Project Advisory Council can consist of volunteer individuals within the project's targeted population and critical community stakeholders will be created during the planning year and maintained throughout the duration of the project. Its purpose can be two-fold: 1) Assure the principles of Self-Determination are driving the activities within the Peer Support Circles (PSCs) and Peer Support Teams (PSTs); and 2) Provide input into the Policy Implications component.

C. Coordinated Support Service Management—A multi-disciplinary approach to client-centered service that can seek to facilitate a continuum of clinical, community and vocational services in a cost-effective manner that enhances service and ensures cost efficiency. It represents a paradigm change to traditional case management.

D. Employment Network (EN)—Federal term for provider agencies that can be registered with a provider (such as Maximus) to deliver specific employment supports and services to individuals activating their Ticket.

E. Future Search—Methodology for bringing together a representative group of approximately sixty-four to seventy-two principal stakeholders (e.g. community leaders) to discuss past, present and future, and arrive at "common ground" that may agree to in a specific of focus. In this case "common ground" can focus on employment for SSI/SSDI beneficiaries.

F. Individual Development Plan (IDP)—A dynamic comprehensive plan developed by the participant, Learning Coach, family members (at client's election) and a Support Service Group Coordinator who can delineate the participant's overall individual clinical, community and employment goals and the services required to meet those goals.

G. Individual Plan for Employment (IPE)—An IPE, can be developed by the individual and the DVR Counselor, can be a description of the specific rehabilitation services that are needed for the individual to achieve an employment outcome. The IPE can be designed to achieve the specific employment outcome that is selected by the individual and consistent with the individual's unique strengths, resources, priorities concerns, abilities, capabilities, interests and informed choice; and the IPE can result in employment in an integrated setting.

H. Learning Coach (LC)—A person who can facilitate the activities of a Peer Support Team (PST), Peer Support Circle (PSC) or other Action Learning Team that may be established. The Learning Coach can create a nurturing environment that fosters the ability of the team to draw from its collective strength in helping each individual team member improve their ability to master health related problems and better manage their lives, in positioning themselves for job opportunities. The responsibility of the Learning Coach can extend to at least three peer support teams (PST). Confidential SSA Contract I. Peer Support Teams (PSTs)—The basic functional process and problem solving group in which program services can be coordinated and self-management education and peer support counseling can be provided. Approximately twelve to eighteen participants can comprise each team and the PST process can be facilitated by a "Learning Coach".

J. Peer Support Circles (PSC)—A Peer Support Circle can be a subdivision of a Peer Support Team (PST). It can have approximately four to six members. There can be at least three PSCs in a PST, each functioning as a bona fide Action Learning team, with each team member empowered to self-determine the best personal strategies for improving their life situation. There may be no designated team leader. They can be self-directed teams. Team members can operate as equals, learn from and with each other, reflect on what is being learned from their collective and individual actions, and can provide support to one another.

K. Quality of Life (QOL)—can refer to the sum of all things in an individual's environment or personal make up that influence their life. The indicators can range from good health, to financial means, purposefulness of their existence, support of family and friends, ability to seek and gain meaningful employment, and feeling some confidence in their future. QOL can be holistic and can recognize that a good quality of life may require a number of things to be in place to drive this end.

L. Self Determination—Self-Determination can be a philosophy of daily living focusing on a holistic, consumer-directed approach which can have four overarching principles: (Nerney, T. and Shumway, D., 1996): •Freedom: Choosing where and with whom to live, how to make a living, and with whom to develop relationships. •Authority: Being in control of how one's long-term care dollars are spent. •Support: Arranging public resources in a way that meet the individual needs of a person. •Responsibility: Using public resources cost-effectively. •Confirmation: Recognizing that all individuals must play a major role in the development and implementation of self-determination policies.

M. Self-Management Education—The ability of participants to apply knowledge and practice skills to optimize their health and economic potential, and quality of life in partnership with their peer support and provider teams.

N. Support Service Group (SSG)—A service group within the Coordinated Support Service Model can be comprised of one Support Service Group Coordinator who oversees at least three Learning Coaches in which each coach may be charged with at least three peer support teams. Therefore, each SSG can be composed of one Support Service Group Coordinator (SSGC), three Learning Coaches, one clerical and nine peer support teams containing approximately one hundred thirty five (135) participants in total. This can be the basic service unit in which the primary intervention of Support Service Coordination is provided through Action Learning and services centered on each participant's IDP.

O. Support Service Group Coordinator (SSGC)—A person that can be assigned with the oversight of all services provided in a single Support Service Group which can usually be case management in nature. At least three learning coaches can be accountable to each Support Service Group Coordinator.

P. Support Service Region (SSR)—Each region can represent one demonstration site and there can be two Support Service Regions. Each region can contain two Support Service Groups.

Q. Support Service Network (SSN)—The Support Service Network can be the group of provider stakeholders that make up the basic four constituent service domains: 1) clinical services; 2) educational services; 3) community services; and 4) vocational services.

R. Teams (two teams can be defined as follows:)—1) Task Teams—teams that can have an administrative focus in ensuring that processes are followed, making certain that educational components can be developed and in place, monitoring program progress and recommending any program adjustments, reviewing information flow and tracking evaluative results, and supporting the referral plan for services. 2) Action Learning Teams—In contrast to Task Teams, Action Learning Teams can be managed by the participants themselves, with all team members as equals; these teams (respective participants) can be empowered through self-management education and problem solving skills to participate in the choice of services to improve their health, community integration, enhance their employment readiness and job placement.

DETAILED DESCRIPTION

While the specification concludes with claims defining the features of the embodiments of the invention that are regarded as novel, it is believed that the method, system, and other embodiments will be better understood from a consideration of the following description in conjunction with the drawing figures, in which like reference numerals are carried forward.

As required, detailed embodiments of the present method and system are disclosed herein. However, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiments herein.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "program" as used herein, is defined as system of services, opportunities, or projects, generally designed to meet a social need. In some embodiments, a computer readable medium can be implemented in software for performing the method steps. The software may be embodied in an article of manufacture that includes a program storage medium such as a computer disk or diskette, a CD, DVD, RAM, flash memory, or other computer memory device. The machine-readable storage can be encoded with a data structure that defines structural and functional interrelationships between the data structure and the computer software and hardware components which permit the data structure's functionality to be realized.

Embodiments of the invention herein present a coordinated health and human services management program that provides a collaborative environment between clinical providers, community service providers, clinical and social service researchers, clients and their families. In one aspect, the management program can be deployed using an information technology (IT) platform but is not restricted to such an embodiment. The web-base IT platform is presented merely to describe one possible implementation of the business methods of coordinated health and human services. The management program can be the application and deployment of a set of business methods that when combined together provide a coordinated and holistic health care service. In practice, the program can educate clients, also herein referred to as participants, to manage disability and chronic disease which includes the related disabling conditions associated with the chronic illness. In one aspect, the program can focus the client on their functional and psychosocial needs for re-entering the work force and the community. The program can be a population-based, client-centric strategy that combines self-management skills with a comprehensive continuum of services to facilitate a community integration and re-employment of the client. The services can include clinical, educational, community, and vocational services. The program can integrate the service offerings to provide a holistic and nurturing atmosphere to treat an entire health condition such as chronic illness. The program can include intervention programs to elevate self-esteem and a sense of participant self-worth. The services can be customized to the client's individual needs and dealt with in a caring environment where learning is encouraged. In one particular example, but not herein limited, the program may target disenfranchised or minority communities and the veterans population with, or at-risk for, chronic disease and disabilities.

Referring to FIG. 1, a coordinated health care and human services management program puzzle 100 is shown. The puzzle 100 can be interconnected through a set of business methods that integrate various health and human services programs. For example, the puzzle 100 can include a healthcare management service program 110, a self-management service program 120, a community and vocational service program 130, an outcomes research service program 140, and an IT platform 150 serving as a coordination unit between the services 110-140. The pieces of the puzzle are shown merely to illustrate the connection of services through a set of underlying business methods. The services 110-140 are depicted as pieces of a "care management puzzle." In one arrangement, the individual pieces can be connected and enabled by the IT platform 150, which can combine access to the services for coordinating and managing the services within the puzzle 100. The puzzle 100 is not limited to the connections and interconnections shown, and can include combinations thereof in various arrangements. The puzzle 100 can link these services with other services, consolidate data from the services 110-140, collect and analyze healthcare outcomes, and develop and refine clinical protocols from client health care data. In one aspect, data from the services 110-140 can be normalized and analyzed to develop outcome health care studies for evidence-based healthcare programs. In practice, the business methods underlying the puzzle 100 can provide a population-based, client-centric approach that facilitates a focusing of a client's functional and psychosocial needs on community integration and re-employment through the coordination and interaction of the services 110-140.

The underlying business methods of the invention provide a broad array of integrated services which can be implemented by means of the information technology platform 150. For example, one business method can capture clinical and cost data from "real-time" clinical and community-based social and vocational services, including protocol-driven clinical trials. The method of doing business can provide the continuity, consistency and efficiency to integrate and synchronize the disparate delivery services 110-140 into a single coordinated information stream. The methods of doing business can improve the participant/provider relationship by providing a healthcare client with access to up-to-date information pertinent to that client's particular healthcare treatment plan. In one embodiment, an open access environment can be provided through an IT platform to enable a joint decision-making process between a healthcare recipient and his/her healthcare provider(s) for the course of that healthcare treatment.

In another aspect, the methods of doing business coordinate phases of a traditional episodic delivery system. For example, health care data from each of the services 110-140 can be captured and made accessible, for example, using the underlying information technology platform 150. Business methods implemented by the information technology platform 150 can capture and archive disparate data from the services 110-140 and can normalize the data to produce outcomes from a clinical, economic, clinical research and community service perspective for improving standards of practice. Whereas healthcare outcomes are conventionally obtained from manually retrieved clinical and economic indicators, the outcomes herein can be automatically processed using the business methods described herein.

In certain arrangements, but not herein limited too, the coordination of the human and health care services and delivery through the business methods can be implemented within a web-based platform; for example, an intranet or extranet platform, an education tool, a tele-health monitoring system, or a clinical research tool. Those skilled in the art can appreciate that the web-based platform provides an integrated healthcare service to improve the quality of life of a participant by consolidating disparate service programs which would otherwise be unavailable as a single personalized health care information source to the participant. The underlying business methods link services 110-140 and consolidate the data for each respective service to enhance healthcare, vocational, and social service delivery outcomes and health care provider protocols. Integration of the business methods for providing a coordinated human and health care services and delivery program can include numerous services other than 110-140 which are contemplated herein.

Figure 2:
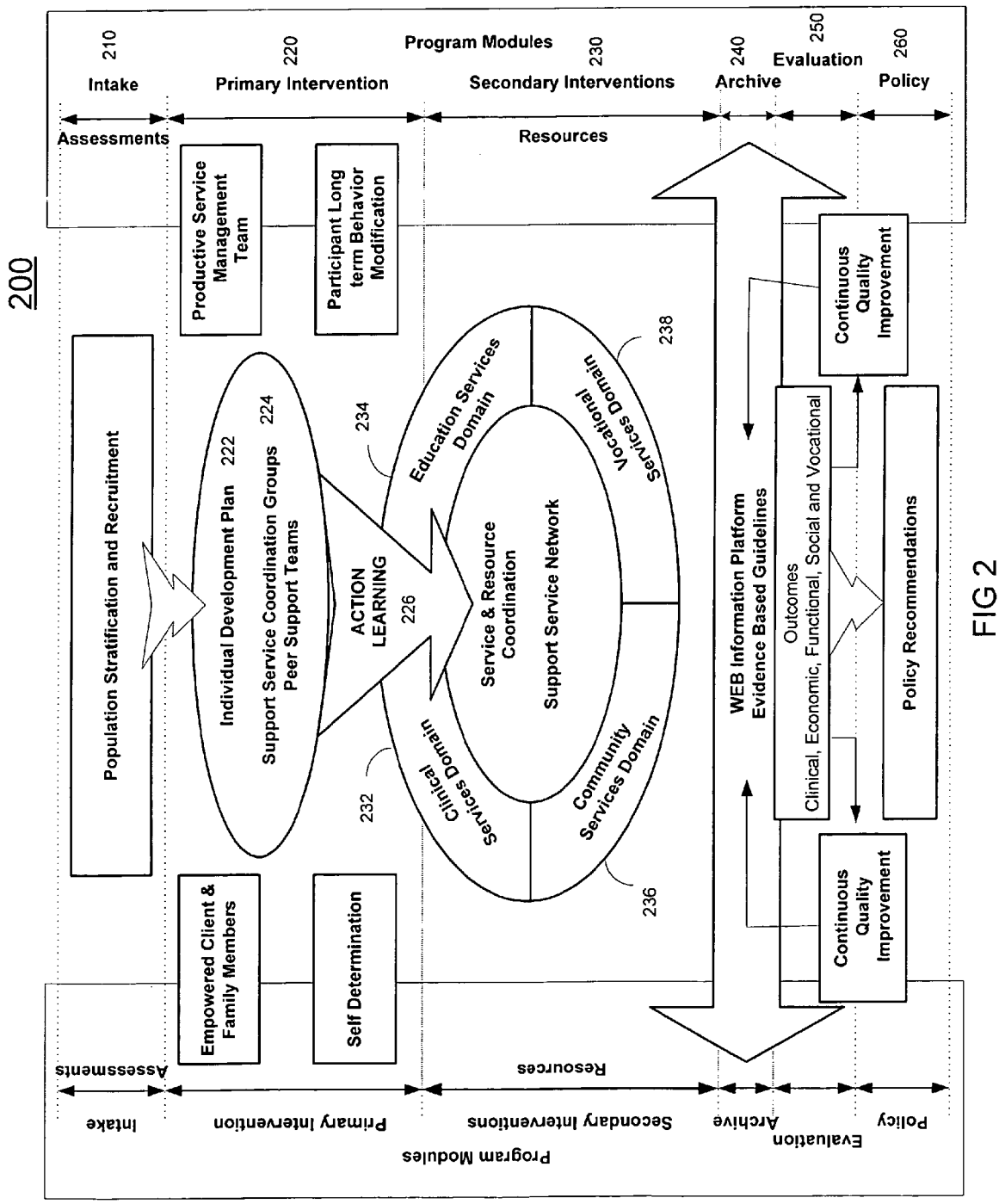
FIG. 2 illustrates a coordinated service delivery network in accordance with an embodiment of the inventive arrangements.

Referring to FIG. 2, a coordinated service delivery network 200 for coordinated health and human services management is shown. The coordinated service delivery network 200, can include an intake assessment and recruitment module 210 for population stratification and recruitment of clients having chronic disease or disability, a primary intervention module 220 for developing an individual development plan and for enacting action-learning through peer support team intervention, a secondary intervention module 230 for providing coordination of services through an information technology (IT) platform, and an information archive 240 to coordinate services for monitoring and tracking client progress. The coordinated service delivery network 200 can further include a an Evaluation module 250 and a Policy module 260. The Evaluation module 250 can contain a Program Analysis and an Individual Outcomes Study Development. Notably, the implementation of the coordinated health and human network 200 relies on the Individual Development Plan (IDP) 222, the Support Service Coordination Groups (Peer Support Teams) 224, and the Action Learning 226.

Figure 3:
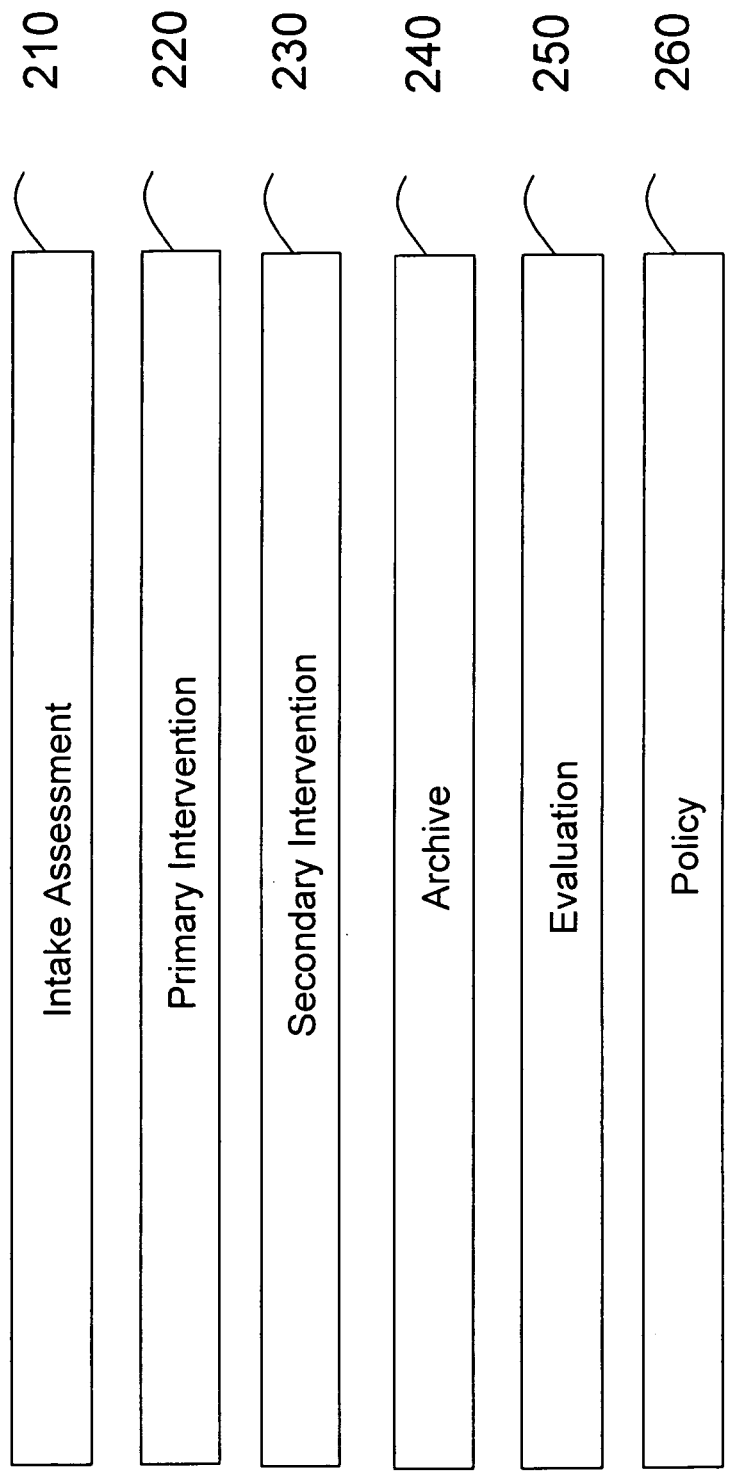
FIG. 3 illustrates a coordinated service delivery network in accordance with an embodiment of the inventive arrangements.

Referring to FIG. 3, the modules 210-260 of the coordinated service delivery network 200 are shown. In some embodiments within the contemplated scope herein it may be useful to access the information archive 240 (i.e. web-base IT platform) for various purposes. One such purpose may be for evaluating client outcomes as shown in FIG. 2. Another such purpose may be for implementing policies based on an outcome. Understandably, the information archive 240 provides various network configurations for interfacing and interacting with the coordinated service delivery network 200.

In one embodiment, the information archive 240 can be an information technology (IT) platform for sharing and archiving information. For example, one method of doing business implements a coordinated services delivery that takes a holistic approach to providing healthcare, wellness, social and vocational services to participants, including overall community integration. Note, the primary intervention module 220 and secondary intervention module 230 provide an environment wherein a team of professionals and "third party" providers utilize Action Learning 226 to maximize their capacity and ability to collaborate with one another. The center of the teams actions is the creation of the IDP 222 that outlines the client's overall plan to realize his or her goal towards of independence.

Understandably, creating an integrated development plan with the participants and/or their family is an integral aspect of the business method. The IDP 222 represents a fulcrum in balancing the "goals" of the participant on one side and "results" of the program on the other. The information archive 240 can measure and report on the outcome of strategies undertaken by the clients and the teams through periodic reviews processes. Understandably, one of the business methods is measuring and reporting the outcome of strategies. The information archive 240 allows for the capacity to collect long term clinical, behavior and compliance information to evaluate long term study outcomes. Understandably, one of the business methods is collecting long term clinical, behavior and compliance information to evaluate long term study outcomes.

The connection of the pieces of the puzzle 100 in FIG. 1 can provide a seamless, efficient, and cost-effective integration of the services 110-140 for supporting the coordinated service delivery network 200. One business method includes constructing a coordinated service delivery network among stakeholders of the program using information technology and team building with "Action Learning" principles as a primary tool to facilitate the integration of services. Action-learning is a primary tool which allows clients and peer support teams to interact and learn from one another. In one aspect, a method of doing business consolidates healthcare and wellness services, educational services by employing action learning, vocational services such as employment networks, and social services. The business methods coordinate access to healthcare, social and vocational services for persons with chronic disease and disabilities thereby facilitating community integration, and, accordingly, an improved quality-of-life for the client. The business methods take the client beyond his or her traditional role of being the passive recipient of services to becoming an active partner in the decision-making processes that can be required to effectively manage his or her comprehensive personal service plan.

In one aspect, the coordinated service delivery network 200 is an evidence-based, population-based model that delivers health care relevant services customized for a targeted population consistent with the demographics and epidemiology of that population. The Community healthcare/vocational/advocacy workers can be placed at the core of the service delivery model, relying upon the confidence building personal relationships, trust and emotional support established by peer-to-peer counseling, to support care plan compliance and to provide socio-economic support. The business methods can provide specific learning content from periodic peer support team meetings on an interactive basis versus didactic learning. The coordinated service delivery network 200 can employ business methods that monitor progress and provide feedback to program managers and program stakeholders. The coordinated service delivery network 200 can focus on the ultimate goal of improved quality of life for clients, encompassing clinical, social, and vocational measures and outcomes. The coordinated service delivery network 200 can provide a central prescription drug benefit and counseling service, as well as access to appropriate nutritionals based on indications of a clients particular health condition.

In yet another aspect, the coordinated service delivery network 200 can target Ticket to Work assignees to Vocational Rehabilitation. The network 200 can provide active recruitment of eligible Ticket holders that have activated their Ticket and have been assigned to a Division of Vocational Rehabilitation. The network 200 can assign a pool of eligible Ticket holders in accordance with the number of participant slots available in intervention and control groups. The network 200 can provide a support service coordination system that is consumer-driven using a peer supported "Action Learning" 226 approach to coordinate, advocate and manage services. The network 200 can provide a peer supported process of Action Learning 226 for interactive problem solving to improve long term "Lifestyle" changes and promote consumer empowerment. The network 200 can provide a comprehensive and coordinated network of support services, such as primary healthcare, community integration, job readiness and placement through an integrated service network. In one arrangement, the network 200 can provide partnership with state sponsored programs through an underlying network connection to maximize all program outcomes. The network 200 can interface to a web based IT platform can capture, analyze, and process program data to promote communication among all critical stakeholders.

Figure 4:
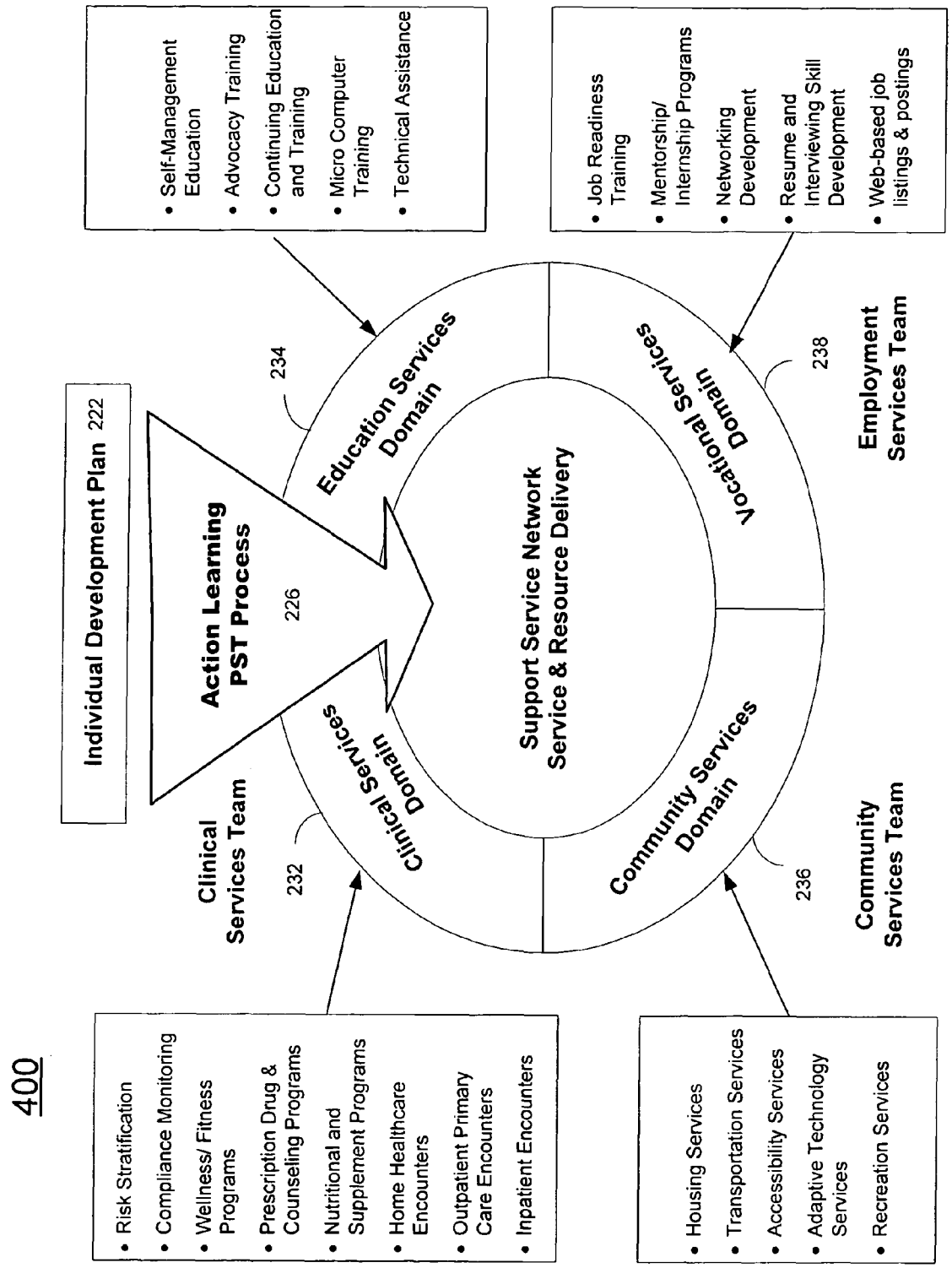
FIG. 4 illustrates a support service network in accordance with an embodiment of the inventive arrangements.

Referring to FIG. 4, service domains under the coordinated health and human network 200 of FIGS. 2 and 3 are shown. The service domains include a clinical services domain 232, an education services domain 234, a community services domain 236, and a vocational services domain 238. Embodiments of the invention are not herein limited to providing only these service domains. In addition, all the modules in each domain do not have to be a part of each program application. For example, a wellness and prevention model application can be created from three of the domains excluding the employment domain. The domains and functional modules associated with each domain can employ business methods that accommodate several program applications. In one aspect, but not herein limited to, the network 200 can employ business methods that offer a unique opportunity and research platform to conduct clinical research for chronic disease population among underserved, underinsured and/or minority populations.

The clinical services domain 232 can employ business methods that include risk stratification, compliance monitoring, wellness/fitness programs, prescription drug and counseling programs, nutritional and supplemental programs, home healthcare encounters, outpatient primary care encounters, and inpatient encounters. The education services domain 234 can employ business methods that include self-management education, advocacy training, continuing education training, micro-computer training, and technical assistance. The community services domain 236 can employ business methods that include housing services, transportation services, accessibility services, adaptive technology services, and recreation services. The vocational services domain 238 can employ business methods that include job readiness training, mentorship and internship programs, networking development, resume and interviewing skill development, and job listings and postings. A description of the four categories follow:

The clinical services domain 232 can employ business methods that coordinate clinical services through outpatient, wellness/exercise, home and inpatient encounters. The clinical services domain 232 can employ business methods that are centered on prevention and wellness in combination with the Individual Development Plan 222. The clinical services domain 232 of the program can employ business methods that coordinate clinical services through outpatient, wellness/exercise, prescription drug services and counseling, home and inpatient encounters. Most program participants (i.e. clients) qualify for private healthcare benefits or public healthcare benefits including Medicare or Medicaid or dual eligibility. Each participant can expected to have or be given the opportunity to select a primary care physician. Physicians can share clinical information with the Program and portions of this data can be updated in the database. This data sharing can occur with the consent of the client. This information can be part of the client record or the Individual Development Plan. The basic clinical services that are provided in the network can employ business methods that account for risk stratification, compliance monitoring, wellness/fitness programs, prescription drug & counseling programs, nutritional and supplement programs, home healthcare encounters, outpatient primary care encounters, inpatient encounters The educational services domain 234 can employ business methods that teach clients skills such as problem solving and decision making for coping with their chronic illness. The educational services domain 234 can employ business methods that teach clients with chronic disease the skills and confidence they need to manage their disease on a daily basis and to manage the longstanding life impact of the disease through principles of self management. For example, people with a chronic disease having received basic disease-specific education are expected to manage the disease for the rest of their lives. This can be the case for minorities and disenfranchised populations who do not have continuity of healthcare. Accordingly, peer support teams provide a forum for self-management education and advocacy training. The educational services domain 234 can employ business methods that provide prevention education for family members, or friends, of clients with chronic disease and disability. Self management education is the responsibility of all members of the peer support team. Customarily, the physician or primary is responsible for informing the client on how to manage their chronic illness. However, rarely will there be time in the average client encounter to adequately provide such instruction. The educational services domain 234 can employ business methods that provide a team approach including clinical experts, nursing and other disciplines to provide client and family education.

The education services domain 234 can employ business methods that promote self-management education, advocacy training, continuing education training, micro-computer training, and technical assistance. The self-management education can be community-based which differs from traditional self-management education in several ways. First, it can be based on problems identified by the participants, where needs drive program content. Second, program content focuses on imparting skills such as problem solving and decision making. A purpose of the education is to prepare program participants to have the skills and confidence to manage their disease on a daily basis, as well as to manage their life roles and emotions. Judgment about the quality of the education can be based on improvements in key health, functional, productivity and lifestyle outcomes. The outcomes may be both physiological and psychological having a direct impact upon quality of life.

The community services domain 236 can employ business methods that promote housing services, transportation services, accessibility services, adaptive technology services, recreation services which provide activities for client's daily living. Understandably, the community services are offerings available from the community to the client to assist the client with their daily living. This can include physical and occupational therapy, physical environment services and accessibility training, and transportation accessibility, housing services, transportation services, accessibility services, adaptive technology services, child care, and recreation services. Moreover, technical assistance by benefits and financial counselors can be provided to train and assist clients to better navigate the various reimbursement and payment systems for improving personal financial planning. The community integration section employ business methods that can capture primarily employment information from vocational assessments, including resumes, internship and mentorship opportunities, job postings and job retention data. In addition, it contains local and regional community services resources. Community services can be coordinated and/or facilitated through a Support Service Group (SSG) Manager through a respective Peer Support Team.

The outcome of these facilitated services can be based on the ability of each client to live and function independently and to successfully re-integrate into his/her respective community, to the fullest extent possible. The measure of these outcomes can be self-reported levels of physical activity, directed at increasing participants' ability to perform basic tasks of daily life, including participation in community-based activities. Community services within the IDP 222 may be unique with milestones that address both real and artificial barriers to employment and community integration.

The vocational services domain 238 can employ business methods that promote job readiness training, mentorship and internship programs, networking development, resume and interviewing skill development, and job listings and postings. Understandably, a primary outcome of the program is gainful employment facilitated by a coordinated continuum of services that provides job readiness training and community integration services. In one aspect, the program can employ business methods that facilitate and enhance employment opportunities for the program participants in partnership with divisions of vocational rehabilitation and associated employment network collaborators. Each participant can prepare for employment opportunities through the mechanism of a Peer Support Team (PST), including: vocational assessments, job readiness training, job mentor ships and internships, employment referrals, follow-up and employment retention, though are not limited to these. Moreover, participants may also be trained and supported in learning how to identify and pursue their own employment opportunities.

The vocational services domain 238 can employ business methods that provide basic services including job readiness training, mentorship/internship programs, networking development, resume and interviewing skill development, job listings & postings. Understandably, a primary outcome of the Program is to facilitate a coordinated continuum of services for helping a client ensue gainful employment opportunities. Business methods include organizing peer support teams help a client prepare for employment opportunities which include: vocational assessment, job readiness training, job mentorship, employment referrals, follow-up, and employment retention. In one arrangement, the program can employ business methods to collaborate directly with both public and private placement agencies to facilitate employment. For example, a platform includes an employment section to post client resumes, and job postings that are actively recruited from the local community. The vocational services domain 238 can employ business methods that create a virtual job fair within the IT platform. Understandably, preliminary communication and information is exchanged with potential employers using the IT platform.

Program participants' vocational and employment efforts can be coordinated with a provider such as a division of vocational resources (DVR) and/or an employer network (EN) to support their final employment goals. The coordinated health and human network 200 can employ business methods that promote for the collaboration with DVR and ENs to develop partnerships with local employers, business advisory councils and other relevant community providers in order to improve employment outcomes. These collaborations can also be developed to improve employer awareness of employment for persons with disabilities. Within the vocational services domain, participants can be provided basic microcomputer skill training and computer access in a classroom environment.

For example, the skill training can promote each participant's job readiness skills with basic word processing, spread sheeting, database and communication skills. Additionally, it will give each participant the ability to access their respective program files, input information, review calendar of program events and communicate with program stakeholders. The vocational services domain 238 can employ business methods that promote an employment section to post client resumes, as well as job postings for providing active recruitment from the local community. In one aspect, the vocational services domain 238 can employ business methods that create a virtual job fair. For example, preliminary communication and exchanges of information can even be executed over this platform with potential employers by the prospective employee(s).

Embodiments of the invention also concern a program 500 (i.e. method) for coordinated health and human services delivery through an information technology (IT) platform. When describing the program 500, reference will be made to FIGS. 1-4. Moreover, the steps of the program are not limited to the particular order in which they are presented in FIG. 5. The program can also have a greater number of steps or a fewer number of steps than those shown. The program 500 can include assessing and recruiting clients 510, developing an individual development plan for clients 520, supporting service groups and managing services for clients through action-learning and peer support team intervention 530, sharing and archiving information for monitoring and tracking client progress 540. In a first arrangement, the program 500 can further include delivering the services through an IT platform for providing on-line access 550, and analyzing and measuring the effectiveness of the coordinated service delivery program 560 to provide healthcare, community integration, and employment services to the client. In a second arrangement not shown, the program 500 can further include collecting outcome performance indicators for evaluating them against those collected from a control group. The program 500 can also include providing policy implication recommendations.

In one embodiment, the program 500 can provide a consumer driven/client-centered approach that involve the client as an active team member stressing self-determinant collaborative goal setting for improving client-provider participation and interaction. In another embodiment, the program 500 can provide a service delivery extension to traditional medical and wellness care that links social and vocational services to facilitate community inclusion in addition to fundamental clinical and economic goals. In another aspect, the program 500 can be deployed within a special needs community such as SSDI and SSI beneficiaries (or populations) for providing services to a disenfranchised, disabled, or minority populations at high risk for chronic disease and its co-morbidities, and consequent disabilities.

The program 500 can extend service delivery beyond traditional medical care to link community and vocational services thereby facilitating community inclusion in addition to fundamental clinical and economic goals. The business methods of the program 500 can provide implementation for a client-centered model improving upon client-provider interactions by involving the client as an active program team member and stressing client-centric collaborative goal setting. The program 500 can apply principles of Action Learning as the underlying process to promote behavior modification and lifestyle change. In this aspect, the methods of doing business can place peer support teams at the core of the service delivery model, relying heavily upon the personal relationships, trust factor and emotional support established by peer-to-peer counseling, to IDP compliance to enhance gainful employment opportunities.

In one arrangement, the program 500 can be implemented through an IT platform, which coordinates and maintains connectivity of services and overall communication among program stakeholders. In practice, an IT platform can implement the program 500 to provides seamless, efficient, and cost-effective facilitation of health care delivery features as one implementation example. Another implementation example can be an intranet or extranet platform. The IT platform can enable definitive data capture to validate program premises by measuring and analyzing program indicators/ metrics. Understandably, business methods include capturing data and validating program premises. The business methods underlying the IT platform can allow for the development of a new and different perspective on outcome development by combining data analysis results from healthcare to community and vocational services allowing for the opportunity to develop new cost/economic models. It should be noted that the program 500 can be implemented by various other applications which may or may not be.

In one application, the program 500 can combine a coordinated, holistic, consumer-directed care approach within an Employer Network, such as a state Vocational Rehabilitation Division. Business methods include partnering with an Employer Network to maximize the support and services available and accessible to project participants. Understandably, the partnership can increase a client's opportunities to increase their independence, productivity, and self-worth. Such partnerships can also increase the research value or program potential for examining future statewide and nation wide policy issues. Business methods can include examining problems and recommending solutions considered from the perspectives of the client or individual, or providers such as the employer networks or the funding agencies such as the SSA, Medicaid, and Medicare.

Figure 5:
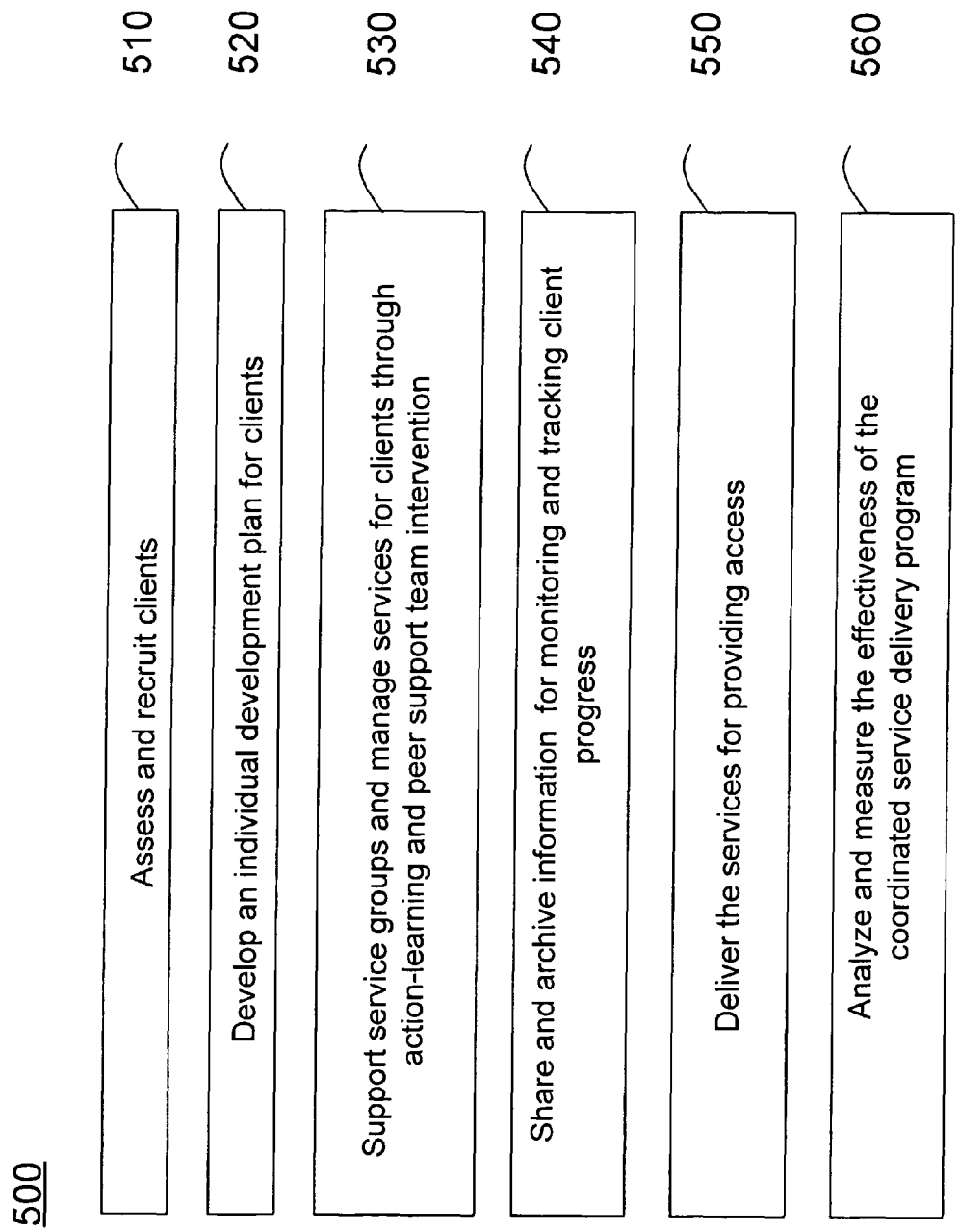
FIG. 5 presents a program for coordinated health and human services delivery in accordance with an embodiment of the inventive arrangements.
Figure 6:
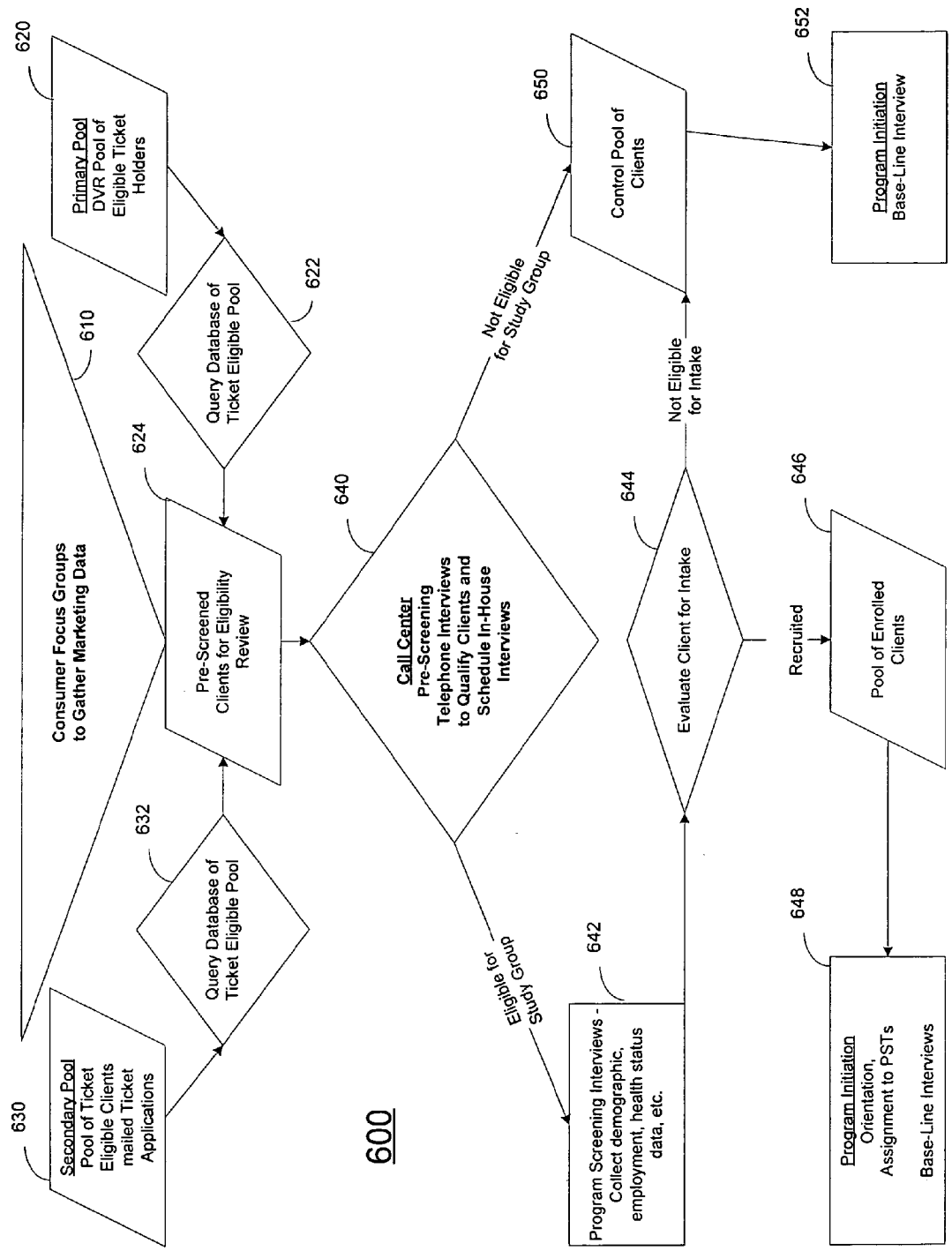
FIG. 6 presents a flowchart for intake assessment and recruitment in accordance with an embodiment of the inventive arrangements.

Referring to FIG. 5, the first method 510 of the program 500 is intake assessment and recruitment of candidates. The intake assessment and recruitment method collects long term clinical, behavioral, and compliance information from clients to evaluate long term study outcomes. This can include analysis of demographic, employment history, prevalence of chronic disease and other health factors, utilization and other risk stratification factors for chronic disease and disability. Briefly, referring to FIG. 6 a flowchart for client intake evaluation is shown. At step 610, consumer focus groups can gather marketing data. At step 620, a primary pool of eligible ticket holders can be identified. At step 630, a database of the ticket eligible pool can be queried. At step 640, clients can be pre-screened for eligibility review. Notably, a second pool 632 and associated database 634 can be queried to identify other eligible candidates. At step 640, a call pre-screening can be conducted to interview identified candidates. At step 650, a control group of candidates ineligible to participate is formed. At step 643, eligible candidates are screened to collect demographic, employment, health care data, and the like. At step 644, clients are evaluated for intake assessment. At step 646, a pool of recruited clients is enrolled in the program 500. At step 648, program initiation begins wherein clients go through a base line interview, an orientation, and are assigned to peer support teams. Clients not selected in the control pool are interviewed at step 652.

Figure 7:
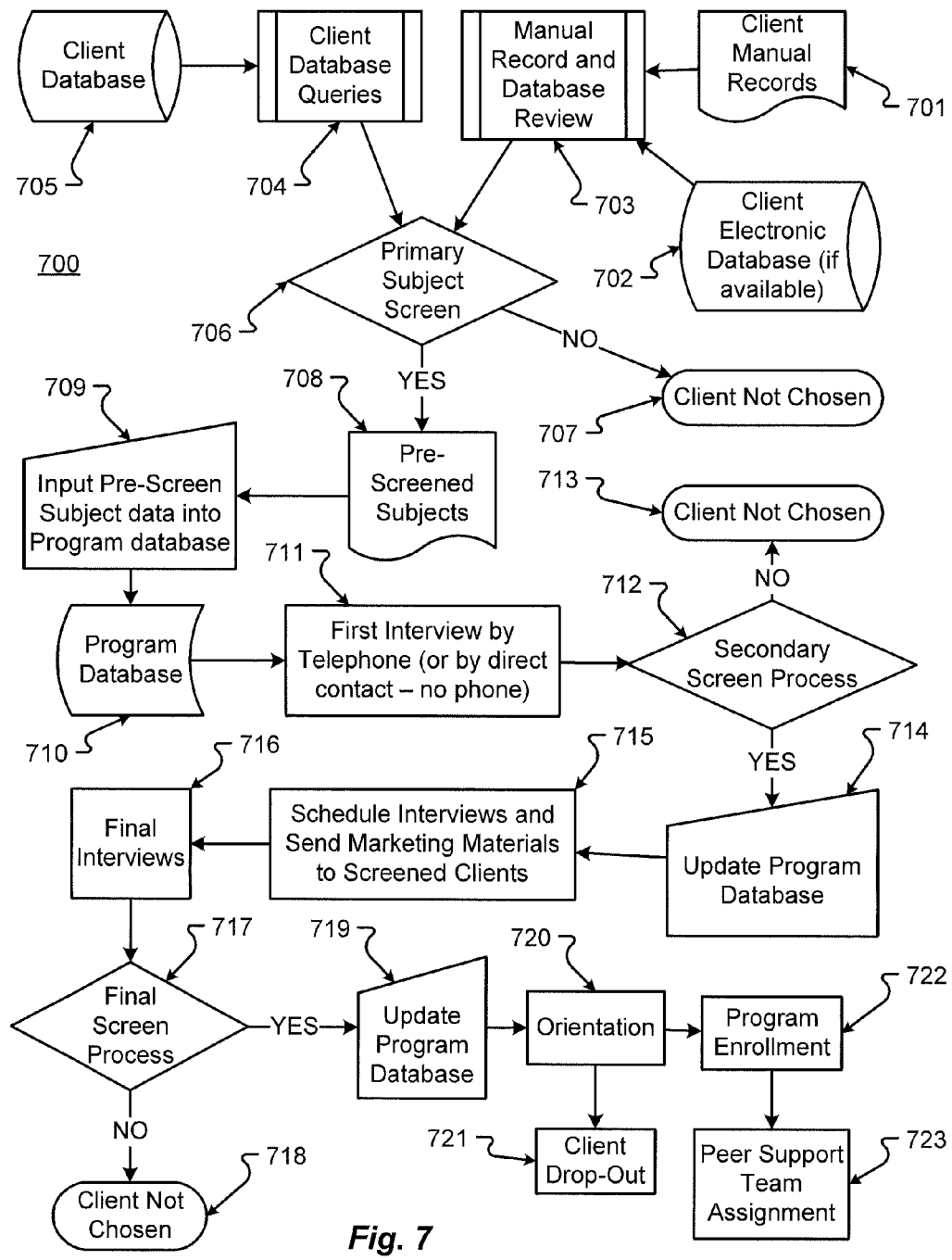
FIG. 7 presents a method for intake assessment and recruitment in accordance with an embodiment of the inventive arrangements.

As a particular example of the intake assessment and recruitment method, a supporting method 700 for assessing and recruiting clients is shown in FIG. 7. The method 700 can also have a greater number of steps or a fewer number of steps than those shown. At step 701, client manual records and client information from an electronic database 702 can be reviewed 703 to generate a client profile. This can include collecting long term clinical, behavior, and compliance information from client records. A client profile describes the health type characteristics for a candidate participant. At step 704, an inquiry can be sent to the database 705 for identifying candidate clients. The inquiry can include analysis of demographic, employment history, prevalence of chronic disease and other health factors, utilization and other risk stratification factors for chronic disease and disability. A profile of client qualification criteria with the support of all program stakeholders can be generated.

At step 706, the client can be subjected to a primary screening. Clients who are not chosen 707 are encouraged to participate in the traditional programs. After the pre-screening process 708, data of selected clients can be input 709 into the Program's database 710. The pre-screened clients can then be interviewed 711 in person where they live, allowing direct assessment of their needs and interest in participation. At step 712, a secondary screen process can be conducted. Prospective clients who are not chosen 713 are encouraged to participate in the traditional programs and are given recommendations if they wish to be considered again for the Program. The clients may be encouraged to participate in parts or selected modules of the Program, if available. The Program database is updated 714, and the qualifying clients can receive program materials by mail and can be scheduled for a "face to face" interview 715 for final screening 717. Final interviews are given, and qualifying clients are finally selected, enrolled 722 in an orientation program 720, and then assigned to a peer support team 723, with team members usually geographically proximate in a neighborhood. Clients that are not chosen 718 or that drop out from the orientation are updated within the program database 719. Clients that are not chosen are encouraged to participate in a traditional program and are given recommendations if they wish to be considered again by the proposed Program In one practical example, the intake assessment and recruitment module 210 of FIG. 2 can be applied to recruit Ticket to Work beneficiaries. Understandably, the module 210 can include developing a profile of client qualification criteria for recruiting clients and receiving approval and support from program stakeholders. Tickets to Work beneficiaries, however, have been historically skeptical in participating. In general, eligible beneficiaries have had no interest in returning to work, and they can be highly distrustful of government programs. Understandably, eligible beneficiaries do not want to risk loss of their existing benefits and are not interested in risking loss of this safety net once in place. Eligible beneficiaries consider return to the workforce, if physically and mentally able, and perceived as significant gain and life improvement. Their mental outlook can directly impact the ability the program's ability to recruit these populations. The co-morbidity of depression is often present, and some have lifestyles, including diet, that work against their health and sense of general well being. Existing services are difficult to access and are compartmentalized and fragmented, and therefore difficult for the eligible beneficiary to navigate.

Very few of those beneficiaries recruited have actually returned to the workforce. Accordingly, the program 500 includes a recruiting strategy within the intake assessment and recruitment module 210 of FIG. 2 that overcomes these barriers. The business method strategy includes recruiting upbeat and non-bureaucratic individuals, focusing on building the level of trust in dealing with program staff, assessing what is impacting the lives of those being recruited, planning to the sensitivity of challenges faced by counselors in working with the beneficiaries, and providing marketing strategies that are the product of joint deliberation between vocational rehabilitative teams and managers. The intake assessment and recruitment module 210 includes business methods that identify which beneficiaries are selected as participants for the coordinated health and human services delivery program.

Referring back to FIG. 5, the second method 520 of the program 500 is primary intervention wherein an individual development plan (IDP) can be developed, peer support teams can be formed, and action learning can be applied. Understandably, the method 520 includes developing an individual development plan for clients, forming peer support teams, and applying principles of action learning. Notably, the IDP is the distillation of the overall plan of the client's goals and aspirations benchmarked against the real possibilities of achieving the documented personal goals. In essence, the IDP is the "fulcrum" upon which the realization of program goals rests. Action-learning is the overall climate by which the IDP is processed. The combination of the IDP, as the critical client tool or plan, with action-learning, as the model process with its interactive, team-building, empowering and self determinant qualities, and finally the secure use of the Internet to communicate and share information make a unique service delivery program 500.

Referring back to FIG. 2, the primary intervention module 220 can include business methods which help each client create an Individual Development Plan (IDP) 222 in concert with family members, peers, and other program stakeholders. The IDP 222 can be a multifaceted document that provides the clinical background and life history of the client. For example, the IDP 222 can contain education, training received, family information, and employment history of the client, but is not limited to these. The IDP 222 can include demographic information, health status information, community information, social services information, vocational information, and employment information. The IDP 222 can be used as a roadmap to balance the goals of the client with the program results.

The IDP 222 is the client's service management record. Most importantly, it is the documentation and progress record of the program goals that the client hopes to achieve. Participants lay the ground work for their IDP 222 by determining goals that they choose to pursue, whether they relate to health, fitness, self-confidence building, employment or other areas. The IDP 222 becomes the prime vehicle for tracking progress and reviewing indices that relate to improved health and general well-being. It is used to monitor progress in pursuing employment related goals. Notably, the information generated can be held in strict confidence. Families can be encouraged to be a part of the process, subject to the approval of the participant.

The primary intervention method 220 can coordinate the exchange of information between a client and a peer support team 224 composed of a group of individuals that together help the client with community integration and re-employment. The client and the peer support team participants learn from each other through action learning. Action-learning is a primary tool within the primary intervention module which allows clients and peer support teams to interact and learn from one another. The monitoring and implementation of the individual goals within the IDP 222 includes the use of these peer support mechanisms which is central to the primary intervention module 220. As part of Action Learning 226, the process focuses on the use of Peer Support Teams and Peer Support Circles which includes teams of professionals and third party providers such as specialty physicians or government programs to help define client qualification criteria. The primary intervention method 220 provides an environment by which interactive information can be communicated, shared, and archived.

Notably, the coordinated human and health service delivery program 500 sets out to promote lasting behavioral changes in the life of the participants, whether it is greater discipline in managing medications, better diet, weight control, or other health indicators. The delivery program relies on Peer Support as the foundation. Participants are encouraged to adopt new positive ways of thinking. Because the program is self directed by participants in terms of taking control of their own lives, the degree of buy in can greatly exceed traditional government programs that flow from a less empowering authoritarian model. Taking action is not an end all. Once action is taken the individual needs to reflect on what has been learned, and how to sustain the change involved. Action Learning requires a balance between action and reflection if deep learning, of the kind that can lead to behavioral change, is to occur. A Learning coach facilitates this balance. Participants share what has been learned with other members of a peer support team (PST) and a peer support coach (PSC).

Figure 8:
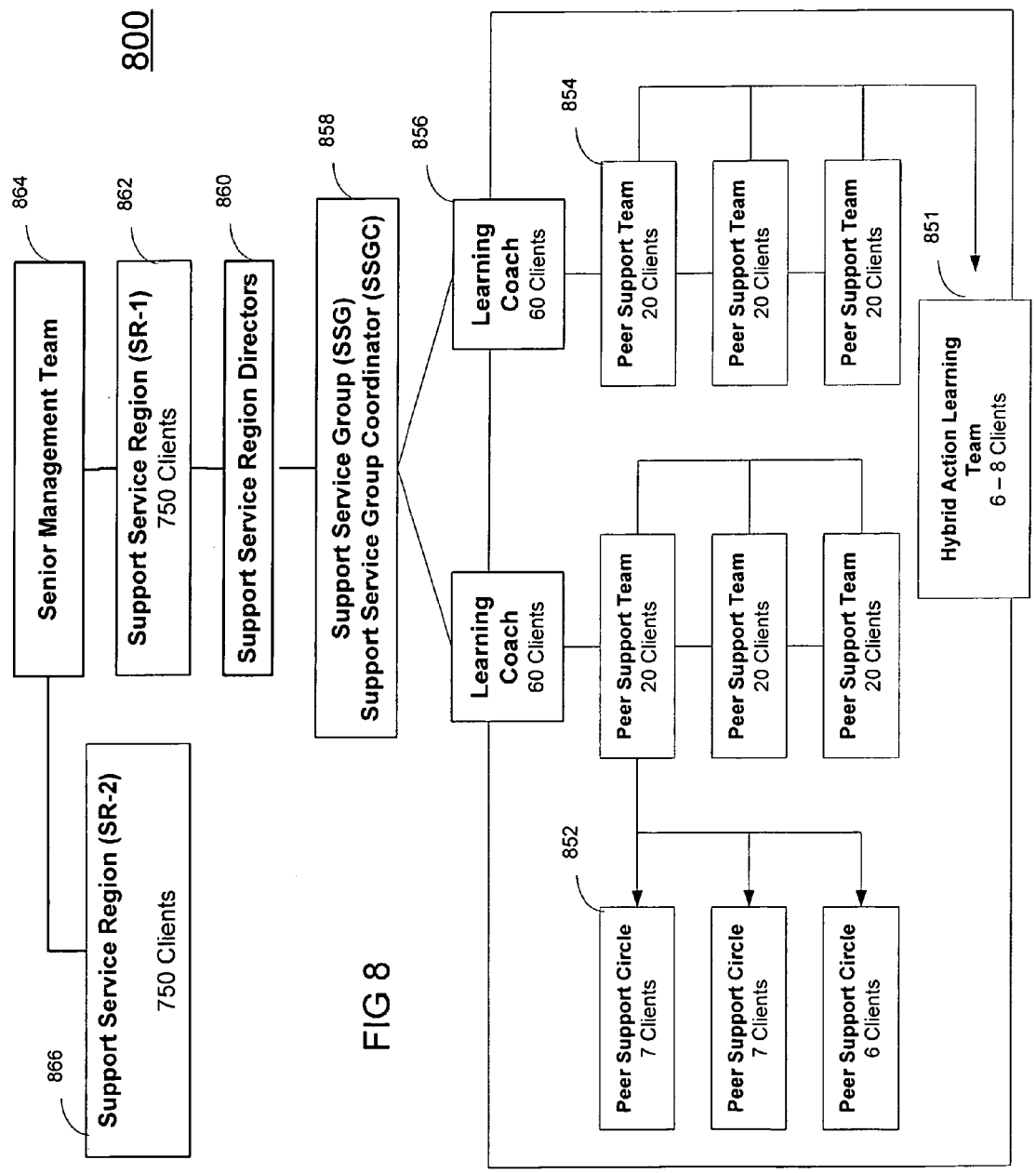
FIG. 8 illustrates an organization chart in accordance with an embodiment of the inventive arrangements.

Referring to FIG. 8, a hierarchy of program stakeholders, participants, and clients is shown. Within each support service group 858, one client delegate can be chosen by each peer support team to serve as a delegate to serve on an Action-learning support service group team with one learning coach 856 from that support service group acting as facilitator. The peer support team 854 can be further divided into three working Action-learning groups or peer support circles (PSCs) 852 of five members each. Embodiments of the invention are not herein limited to having only three working groups, the PST can have more than or fewer than this number. This team can discuss progress achieved within their respective support service group and provide feedback to promote achievement of client and peer support team goals. Further, these teams can participate in discussions with both provider and employment service teams to enhance client provider and employer relationships. Peer support circles within the hierarchy may have no designated leaders, and participants determine priorities and areas of focus by the help of a learning coach. The coach can also serve as a resource for identifying agencies or programs that can provide support. Together, the peer support team and client employ action-learning principles.

Support service managers within a peer support team can coordinate or facilitate the availability of the community services to the client in order to maximize vocational and quality of life outcomes. For example, an outcome of these facilitated services can be measured as the ability of each client to live and function independently and to successfully re-integrate into his/her respective community, to the fullest extent possible. The measure of these outcomes will be self-reported levels of physical activity, directed at increasing clients' ability to perform basic tasks of daily life, including participation in community-based activities.

In one aspect, the organization chart 800 represents the program support service coordination for the clinical services domain 232. The primary unit of service within this organization chart 800 is the Support Service Group 858. The organization chart 800 includes at least one PSC 852 and one PST 854. At the top of the organization's structure is the Support Service Group Coordinator (SSGC), who is the principal gatekeeper of the Support Service Coordination Group (SSCG) 858. The SSGC 858 supports nine PSTs 854 (approximately 135 participants), and oversees three Learning Coaches 856. This person (857) is the primary coordinator of all program services and resources for those participants in the SSCG 858. The Learning Coach reinforces action orientation by recognizing the achievement of individual members through PST celebrations of success. Progress is also reinforced by actively using the IDP as a vehicle for counseling individual PST members. This can lead to amendment of the IDP.

The three Learning Coaches 856 in the SSCG 858 have reporting responsibilities to the Support Service Group Coordinator (SSGC). The Learning Coach's 856 responsibility is to facilitate three Peer Support Teams (PST) 854 (approximately 20 persons each), as well as the three Peer Support Circles (PSC) 852 (approximately 7 persons each) under each PST. The Peer Support Teams (PST) 854 provide the centerpiece for all processes that occur in the program 500. PST's 854 are guided by the principles of Action Learning. Each PST (12 to 18 members) 854 can be comprised of three Peer Support Circles (PSC) 852 of four to six members each.

The PSCs 852 operate as Action Learning teams which corresponds to the division where the Individual Development Plans (IDP) begin to emerge through the process of mutual collaboration and support. The basic tenets of Action Learning are based on the simple principle of placing people in a safe and trusting environment where they can learn from and with each other. Action Learning provides a confidential and secure environment for interactive dialogue and problem solving. The Learning Coach (LC) 856 does not act as a leader of the team per se, but rather guides the process. The LC 856 facilitates the PST 854 and PSC 852 activities, and works with each participant in developing and managing their IDP. Support Service Coordination is solely managed within the Support Service Group. Service coordination is primarily based on Action Learning driven interactive problem solving whereas participants within each PST or PSC identify problems specific to their respective needs. This process may result in a service referral if the issue cannot be resolved within the PST or PSC. All referrals are made through the Learning Coaches to the Support Service Group Coordinator for validation. The referrals are then ultimately made by the SSGC to a Support Service Network (SSN).

Figure 9:
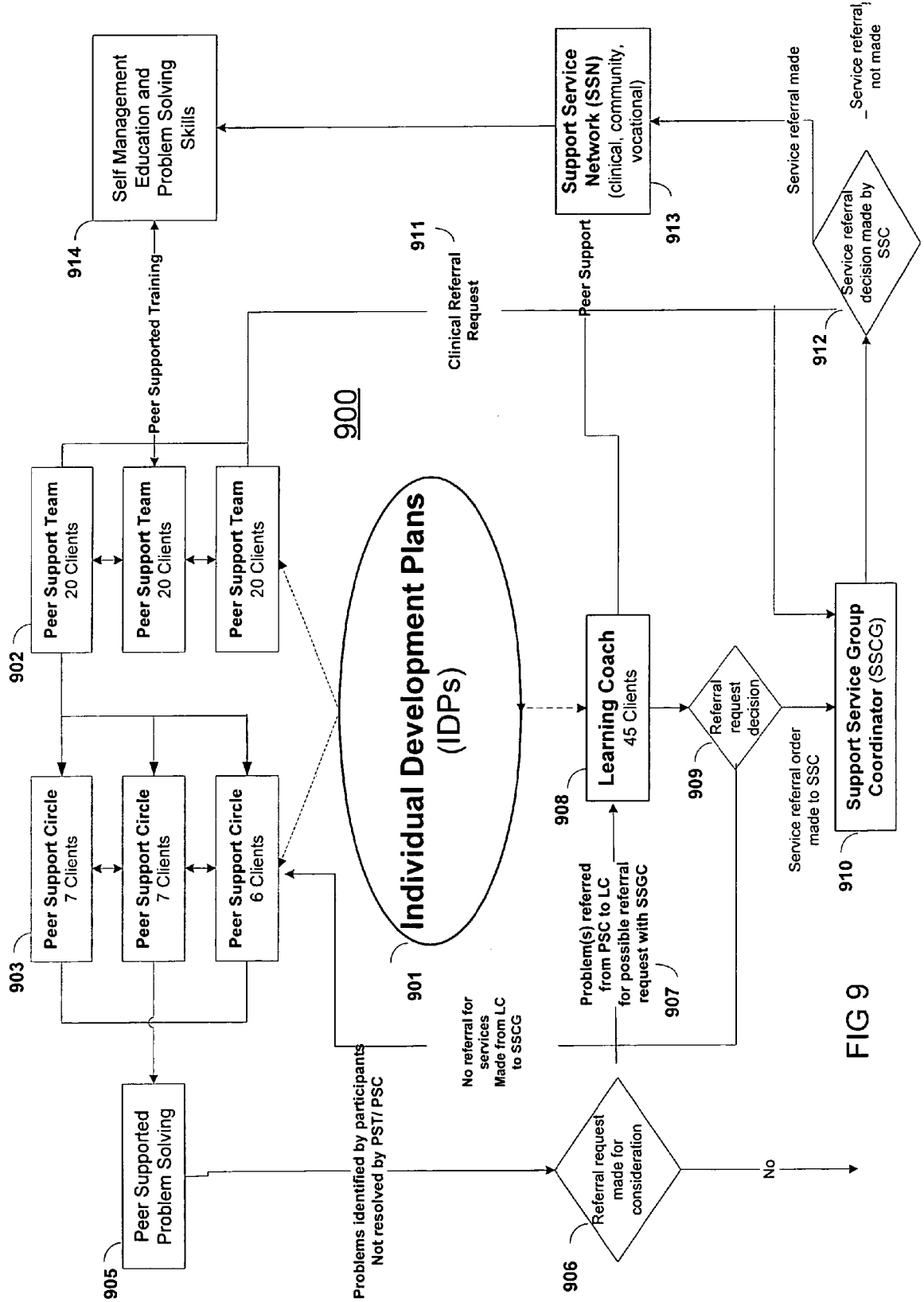
FIG. 9 illustrates a peer support team coordination flowchart in accordance with an embodiment of the inventive arrangements.

Referring to FIG. 9 a support service coordination flow chart 900 is shown. The flow chart 900 identifies the IDP within the center of a peer support network. At step 901, an IDP 222 can be created for a client. At step 902, a peer support team 902 comprising a peer support circles 903 can be assigned to work with the client. At step 905 peer support involvement with the client can help the client identify and resolve health care issues. At step 906, a referral request for consideration can be made. At step 907, problems referred from the PSCs can be assigned to a learning coach 908. The learning coach can refer the decision 909 to a support service group coordinator 910. The service group coordinator 910 can interact directly with the client and the peer support team 911. Accordingly, the support service group coordinator can refer 912 the service decision to the support service network 913. Notably, the support service network can include the clinical, community, and vocational service domains 232-236. The support service network 913 can provide self management education and problem solving skills to the client through coordinated delivery of services 914.

With the assistance of the Learning Coach, the Support Service Group Coordinator serves as the primary gatekeeper of client service coordination. One responsibility of the Support Service Group Coordinator can be to identify facilities, coordinate transportation, schedule childcare, and track client referrals via a web based platform. By monitoring progress versus IDP's across the various PST's, the manager is able to capture critical data for evaluation purposes. This manager also determines the optimal setting for PST meetings, including community settings, such as churches, community centers, health clubs and schools, making sure that the facilities provide lockers and shower facilities to support the fitness component of what occurs as a part of each PST meeting. During the biweekly PST meetings, clinical functional data is collected and a learning delivery process of self-management education and peer support counseling is provided. In this forum, clinical and community services are also provided, including benefits counseling, vocational assessments and job readiness services. Job mentorships, internships and job interviews are coordinated through the PST process and Support Service Group Coordinator in concert with the State Division of Vocational Rehabilitation (DVR) organization and other community stakeholders.

Support Service Group Coordinators work closely with the learning coaches and their respective peer support teams to regularly monitor both self-tested and laboratory tested diagnostics and their social performance measurements or indicators. These managers are responsible for monitoring data and determining, in collaboration with the learning coach, how best to support each client, including clinical follow-up, and educational, community or vocational interventions that are best fitted to the IDP. The Support Service Group Coordinator is also responsible for making sure that all participant data is updated and documented on-line.

In addition to the Peer Support Circle (PSC) 852 within the PST's 854, each Support Service Management Group 858 can have an overall Action Learning team, called a Hybrid Action Learning Team. One "delegate" from each PST 854, democratically "elected" by the PST membership, can serve on this team. This team serves to synthesize and communicate the views and recommendations of all nine PSTs 854 in each pilot location. The Hybrid Action Learning Team provides feedback to the program managers on how the program can be further refined from a consumer perspective. This is another example of the client as the principal focus in this program, a strategy that fosters engagement and buy-in through participation in the seminal processes that guide the delivery systems. In this respect it can underwrite self-determination, empowerment, independence and self-governance. PST delegates can serve as liaisons with their PST's membership for providing real time feedback on discussion of issues, recommendations, and decisions reached. Delegates to the Hybrid Action Learning Teams can also be invited to serve as assistants to the Learning Coaches 856 in maintaining systematic contact with those PSC members who leave the PST 854, either through employment or for other reasons. These delegates can be seen as potential future Learning Coaches 856 based on the leadership traits they demonstrated in being elected as delegates to the Hybrid Action Learning Team 851 and their willingness to accept such service.

In one example, a Support Service Group Coordinator can be a nurse practitioner who is the primary gatekeeper for coordinating all participant services referred to the program. For example, the nurse practitioner can be a SSGC who is responsible for monitoring and reviewing clinical indicators or any data reported as "flags". The nurse practitioner can try to resolve or make the appropriate clinical referrals to the respective care physician. A nurse practitioner can diagnose and prescribe medications, as well as make referrals to appropriate specialists, if necessary; the position in one respect is providing a primary care role.

A team approach can be implemented with the SSGC as the team leader, together with the participants and their family, the Learning Coaches, clinical professionals, as well as other disciplines review clinical and community data to assist in IDP development and assessment. Clinical experts may provide part of the self-management curriculum, although all team members are involved in the self-management education process. As part of self-management education (234), the client can be instructed to monitor chronic disease indicators. These indicators can be tracked and archived within an IT platform and supervised by the Support Service Group Coordinator. Monitoring of such indicators can be a significant factor in complying with the IDP (222). Compliance with the clinical module of the IDP (222) may prevent or reduce acute healthcare encounters, significantly reduce healthcare costs and enhance employment opportunities. Clinical indicators can be monitored during the weekly PST meeting, and documented by entries in daily "Learning Logs", or via telephone monitoring. Acute incidences can be reviewed by the SSGC who may be responsible to resolve all acute and chronic problems either internally or by referral to the primary care or specialty physician.

Returning back to the program 500 of FIG. 5, the third method 530 is secondary intervention wherein service groups and management of services can be supported through principles of action learning. Understandably, the business method 520 includes supporting service groups and managing services for clients through action-learning and peer support team intervention. The program delivery, from clinical services to self-management and community services, can be orchestrated by a multi-disciplinary network of providers including an empowered client that shares in the decision-making process. The Program Team is comprised of all the main stakeholders from the Support Service Group Coordinator, physician, health educator, dietician, exercise physiologist, Learning Coach, vocational counselor, benefits counselor, etc. Productive interactions between the client and the provider teams are enhanced by an empowered client, evidence-based practice guidelines, individual development plan (IDP), and access to clinical and employment data.

The Support Service Network or the continuum of services and resources incorporates four main service activity areas or domains which in one embodiment may be integrated by an IT platform 150 illustrated in FIG. 1. These services are monitored on-line by the Support Service Coordinators. In one aspect, the IT platform 150 facilitates access to all the service data generated by the Program team, as well all provider stakeholders. The IT platform 150 can integrate the primary intervention module 220 and the secondary intervention module 230. For example, the secondary intervention module 230 of FIG. 2 can include a clinical services domain 232, an education services domain 234, a community services domain 236, and a vocational services domain 238. The clinical services domain 232 can include business methods that monitor chronic disease indicators captured during peer support team meetings. The indicators can be archived in a database for complying with the IDP (222). The education services domain 234 can include business methods that provide preventative education for family members of clients with chronic disease and disability. The community services domain 236 can include business methods that support active daily living of clients for overcoming employment and community integration barriers. The vocational services domain 238 can include business methods that facilitate a coordinated continuum of services for providing the client with gainful employment opportunities.

The environment provided by the continuum of services (232-238) guides the client through program modules (510-560) for building their capability to live a full life and find meaningful employment. In order to produce the environment, peer support teams (PST) are organized to enact principles of action-learning to achieve both individual development plan (IDP) and team goals. The secondary intervention module 230 can include business methods that engage peer support teams (PST) to use the principles of Action-learning to meet both individual (IDP) and team goals. Understandably, action-learning facilitates the peer support team intervention based on the premise that people placed together within an environment can learn from and with each other. Understandably, participants interweave action with reflection in learning how to better handle various aspects of their lives which elevates their chance of gainful employment.

For example, referring back to FIG. 2, the clinical services domain 232 can include business methods that collect, archive and analyze most clinical encounters, as well as clinical indicator information captured from client diaries and PST clinical data collection. For example, the underlying IT platform (150) of the coordinated health and human services delivery network (200) can provide the necessary connectivity internally between the PSTs (854), as well as externally to the community service providers or Support Service Network. The underlying IT platform can also provide access to critical resources to all stakeholders including the program participants. The program outcomes can be considered the responsibility of all members of the PST (854). The PST (854) can provide the basic forum for self-management education, advocacy training and overall problem solving. The program can sustain the PST (854) and basic peer support long term as the PST (854) continues during program follow-up and is encouraged to survive beyond the length of the formal program.

Figure 10:
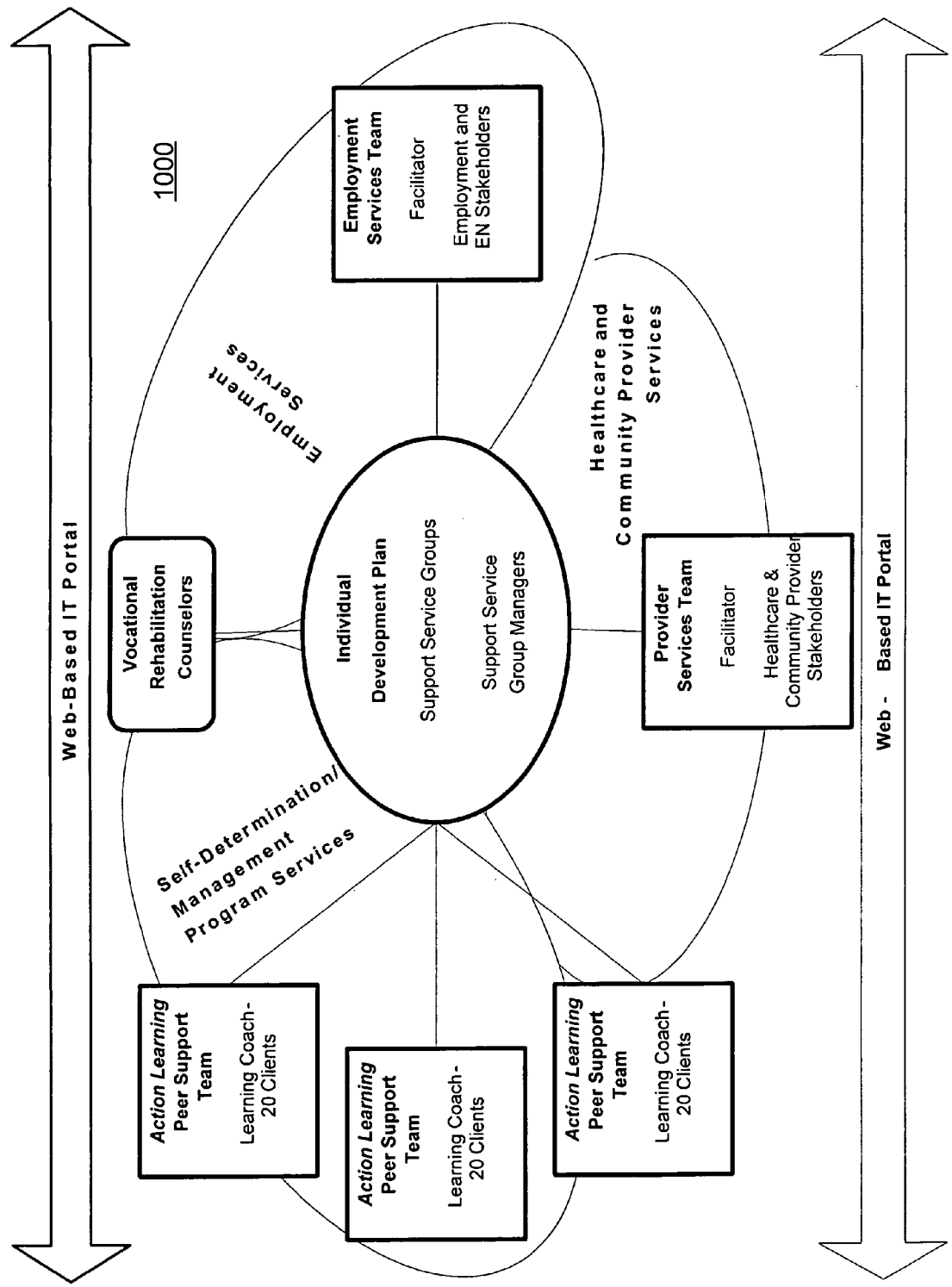
FIG. 10 illustrates a web-based portal in accordance with an embodiment of the inventive arrangements.

Referring back to FIG. 5, the fourth method 540 of the program 500 is sharing and archiving information for monitoring and tracking client progress. Recall, an IT platform (150) can unify the clinical services domain 232, education services domain 234, community services domain 236, and vocational services domain 238. Business methods include monitoring on-line by the Support Service Managers and the PST coaches described in FIG. 8. In one embodiment, such monitoring can be provided through an IT platform 150 as shown in FIG. 10. The IT platform 150 opens access to the service data generated by the program team and other stakeholders though the application of the business methods underlying the IT platform 150.

In one aspect, but not herein limited, the coordinated human and health care services and delivery program helps clients and participants manage chronic disease through applied clinical research programs via an Information Technology (IT) platform 1000. The IT platform 1000 can be a visual tool available on the internet and accessible to clients, their support team, and program shareholders. The IT platform 1000 can deploy a continuum of services within a collaborative network environment that can be monitored by the program shareholders to generate evidence-based healthcare outcomes and protocols for effectively managing chronic disease and disability care. The IT platform 1000 can capture and analyze a client's health care data according to current clinical practice protocols. The IT platform 1000 can implement a health care delivery system based on Action Learning principles that coordinate services to enhance gainful employment by fostering self determination through "peer support" teams and multidisciplinary private/public partnerships which promote the capacity, quality and improved sustainability of healthcare, community service and meaningful employment opportunities. The IT platform 1000 can collect, consolidate and analyze data during the progress of continued and monitored participant health care. This information can be included within the IT platform 1000 of community-based social and vocational services for guiding and helping the client seek gainful employment and community integration.

The platform 1000 can employ business methods to capture, archive, analyze, and disseminate data, and facilitate or integrate stakeholder communication. In general it provides an intranet platform for internal users that include employees, consultants and participants. The IT platform 1000 consolidates data from various information sources that could otherwise remain hidden inside isolated systems, available only to data management staff, and presents the data to all appropriate users from all or most service points in a seamless and user-friendly fashion. The IT platform 1000 coordinates the continuum of services, monitors and tracks client progress by case managers (and other project professionals), develops critical outcomes reports, and ensures optimal treatment and use of program funds. The platform (1000) can contain various algorithms that generate critical outcomes reports and archive information in a data warehouse.

For example, referring to FIG. 11, an outcome report 1100 is shown though section headings, entries, and components of the report 1100 are only shown for illustration. Embodiments of the invention herein contemplate various component arrangements and presentation formats and are not limited to those shown in FIG. 11. Understandably, the outcome reports allow for case or care management results which is a significant function of the platform, in that clients are strictly followed for care plan compliance and for tracking plan outcomes. The IT platform 1000 can be a proprietary program that logistically coordinates the complex continuum of services (232-238) including the monitoring and tracking of client progress by Support Service Group Coordinators (SSGC) and Learning Coaches, or other project professionals. The IT platform 1000 can also provide secure interactive communication and access to proprietary program information.

The information technology platform (150) supporting the IT platform 1000 can comprise both public and private services. The public services can include: 1) general program marketing information, 2) general e-mail, 2) calendar, 3) discussion groups and forums and 4) general job placement information. The private section of the platform is secure and private, and can be divided into two main applications. The first application contains the IDP or participant record including the clinical registry and self-management data. The second application contains community and employment service information.

Referring back to FIG. 5, the fifth method 550 of the program 500 is the delivery process wherein services can be delivered, for example, through an IT platform, for providing on-line access to the client's personalized health care program. The delivery process guides the client through program phases to build their capability to live a full life and find meaningful employment using principles of Action Learning. The program delivery, from clinical services to self-management and community services, is orchestrated by a multi-disciplinary team of experts using Action Learning. The Action learning aspect of the program delivery allows the client to take equal part in the decision-making process of the client's health care plan. Notably, the Program team is comprised of all the main stakeholders including the primary care physician, health educator, dietician, physical therapist, exercise physiologist, support service manager, peer support team coach, vocational counselor, and benefits counselor. In practice, the delivery process provides productive interactions between the client and the provider teams. These interactions are enhanced by an empowered client, evidenced-based practice guidelines, individual development plan (IDP), and access to clinical and employment data.

For example, referring back to FIG. 2, the delivery process module 250 collects clinical and functional data during PST meetings. The delivery process module 250 provides learning delivery process of self-management education and peer support counseling. Within this forum, the delivery process module 250 coordinates clinical and community services and provides benefit counseling, vocational assessment, and job readiness services as part of the IDP (222). Job mentorship's, internships and interviews are coordinated through the PST (854) and Support Service Manager and with other community stakeholders actively involved in the program delivery process.

Referring back to FIG. 5, the sixth method 560 of the program 500 is the evaluation module wherein the effectiveness of the coordinated service delivery program to provide healthcare, community integration, and employment services can be analyzed and measured. For example, referring back to FIG. 2, the evaluation module 260 can capture, measure, and analyze program indicators/metrics to validate merits of the program deployment. For example, the evaluation module 260 can evaluate outcome performance indicators collected from the program such as those from research or intervention group dialogues against outcome performance indicators collected from a control group such as external control. The evaluation module 260 measures outcome performance collected at the conclusion of client participation with those collected during screening and enrollment, the baseline or internal control. This allows the program shareholders to monitor, track, and adjust the services within the program while assessing program performance. For example, upon completion of the program, a client's community integration factors or re-employment statistics are used to determine the program impact.

Outcome performance indicators collected from the intervention group can be evaluated against those collected from the control group (external control). Measures collected at the conclusion of client participation can be compared with those collected during screening and enrollment, which forms the baseline and provides an internal control mechanism. The program can be standardized on specific clinical, social/behavioral and economic indicators or metrics to measure and analyze overall program and individual client performance using validated instruments. The evaluation design comprises: 1) existing instruments, 2) a self-evaluation approach, 3) clinical, process quality of life and economic indicators, and 4) descriptive consumer and service information. The evaluation data can be collected on an ongoing basis, cataloged and organized to conform to the capabilities and potential of the IT platform and interactively analyzed for feedback. Furthermore, results of the evaluation can be presented in an economic framework. Quantitative and qualitative measurements can be analyzed for significant changes and other descriptive statistics.

For example, primary evaluation measures can be based on comparisons to an external control (like-peers) to specifically measure progress (~12 months post enrollment) towards achieving employment goals. Proactive marketing and recruitment can be evaluated to assess the success of the recruitment model. As another example, secondary evaluation measures can be based on comparisons to the internal control to measure progress towards achieving personal/healthcare goals twelve months into the program relative to baseline (IDP). Participant satisfaction can also be assessed.

In another aspect, policy recommendations can be developed. This can include monitoring and analyzing policy implications arising from the enactment of the program. A team of nationally recognized health and disability policy analysts can be put together to review findings, make recommendations resulting from the program, and provide policy implications for review by appropriate federal agencies. The results and recommendations should prove to be valuable for creating policies and guidelines that will assist individuals in finding and maintaining employment while not jeopardizing their health benefits and/or other federal benefits they may be receiving.

In one aspect, a Policy review can be developed to encompass regulatory and legislative matters involving SSA and other proposal related Federal Agencies, the US Congress, proposal-related state agencies and legislatures. A data analysis can also be conducted to focus on how policy alternatives will impact disability and provider organizations. Observations can be made from a retrospective as well as a prospective policy perspective in view of program findings. Notably, SSA has included policy implications in its annual reports to Congress, as it has been called upon by Congress to address policy issues through its Research and Demonstration grants program. Accordingly, the policy recommendations provided by the program may be helpful to SSA in both its legislative and regulatory agenda.

For example, the program can produce findings that have relevance to examining emerging policy implications for the Ticket to Work program. Accordingly, it can be envisioned that individuals selected to participate in the program and that complete the program will have improved job readiness and interviewing skills, improved management and decision-making skills regarding their health options and health status, and have increased their natural circle of community supports and services.

Recommendations can focus on, but are not herein limited to:

1. Regulatory—such as SSA's Ticket to Work regulations (proposed regulations are currently circulating for comment); benefits counseling and disability determinations regulations; HHS' Medicaid Buy-in and other programs; RSA regulations and program guidelines for state vocational rehabilitation agencies and regarding supported employment, Randolph-Sheppard program; and, DOL's One-Stop Program regulations; the Javits-Wagner-O'Day (JWOD) Act program; and
2. Legislative—such as program consolidations and/or coordination; new funding authorizations; reports by any oversight and investigative committees; new research and demonstration programs; new proposals involving employment incentives; and clearer, more directed relationships between the vocational and medical/health communities and programs, to name a few. With less than 1% of these recipients currently returning to the workforce, any demonstrable increase in individuals finding and maintaining employment will be deemed significant in terms of costs as well as reaching the original intended goal of the Ticket—successfully weaning people off of benefits by virtue of placing them back into the job market. Through the use of a control group that is similar to program participants with the exception of our interventions (the project itself), we may also examine findings that can suggest which current policies/practices in place now may actually be barriers to entry into the workforce.

The policy recommendation analysis can address identified fundamental and significant barriers to employment. This can include, but is not limited to: Psychological impact of the disability process, Physical impact of delayed access to health care, Lack of access to training and employment services, Premature loss of benefits, Loss of ongoing employment supports, DI cash cliff and SSI asset limits, Job loss and difficulty of reinstatement, and Work-related overpayments.

Figure 12:
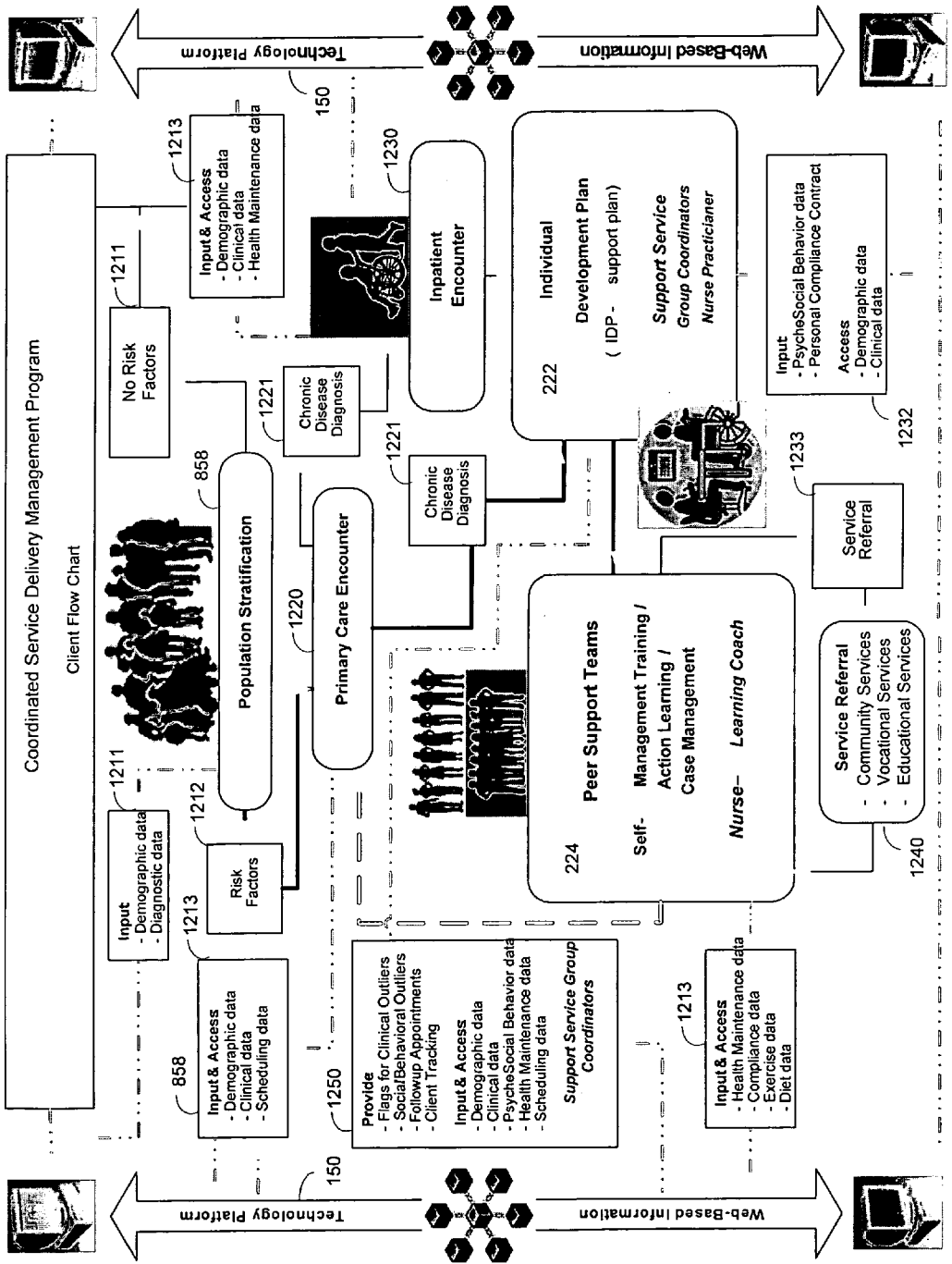
FIG. 12 depicts a client flow chart in accordance with an embodiment of the inventive arrangements.

Referring to FIG. 12, a client flow-chart 1200 for a coordinated service delivery management is shown. Notably, the client flow-chart 1200 illustrates the importance of the two milestone events: the creation of the IDP 222 and the program services 224 which includes self management education and case management that occurs within the peer support teams. Referring back to FIG. 2, the IDP 222 and the Peer Support Teams are primary components for enacting principles of action learning. The client flow-chart 1200 illustrates population stratification 1210 which can include demographic data and diagnostic data as input to the coordinated service delivery management program. Business methods deployed within the population stratification 1210 can include assessing risk factors 1212. The risk factors can be assessed through clinical data and/or health maintenance data 1213. The risk factors 1212 can be carried forward to a primary care encounter 1220. The primary care encounter 1220 can diagnose chronic disease and enter health care data into the IDP 222. A chronic disease diagnosis can lead to an inpatient care encounter 1230. In one arrangement, information gathered from the inpatient encounter 1230 can be provided to a technology platform 150 for presentation. The IDP 222 can be implemented with the participant though the help of support services, group coordinators, and nurse practitioners as discussed in FIG. 8. The IDP (222) can include psycho-social behavior data and personal compliance data as input while providing access to demographic data and clinical data 1232. Data can be captured at baseline and at several intervals during the course of primary care encounter. Notably, the peer support teams (224) provide self-management training, action learning, and case management as discussed in FIGS. 2 and 8. Peer support team involvement can require input and access to demographic data, clinical data, psycho-social behavior data, health maintenance data, and scheduling data 1250. Peer support team involvement can provide flags for clinical outliers, social/behavioral outliers, follow-up action appointments, and client tracking 1250. Peer support team intervention can include service referral 1233 through services 232-238: community service, vocational service, and educational services in conjunction with self management services. Notably, health maintenance data, compliance data, exercise data, and diet data 1213 identified during the action-learning can be provided as information through an information technology platform 150.

A business method for coordinated human and health services delivery has been provided. Notably, there are features of the services delivery model that emphasize distinguishing features over current health care service practices. The model operates within a delineated community (or population), providing services to clients at high risk for chronic disease and its co-morbidities, and consequent disabilities. The model focuses on the overarching goal of improved quality of life for clients, encompassing clinical, social, and vocational measures and outcomes. The model extends service delivery beyond traditional medical care to link community and vocational services, facilitating community inclusion in addition to fundamental clinical and economic goals. The model is an evidence-based, population-based model that delivers culturally-relevant services customized for minority, underserved and underinsured communities with its particular demographic requirements. The model is client-centered improving upon client-provider interactions by involving the client and family members as active program team members and stressing client-centric collaborative goal setting by creating a comprehensive but dynamic care plan, namely an Individual Development Plan or IDP.

In one aspect, the model uses a total systems approach, integrating a comprehensive set of healthcare, vocational, community integration and education services. The model creates and establishes this "Systems Approach" based on collaborations and close partnerships between program stakeholders, providers including consumers and their families. A network of providers is instituted for such services that is coordinated by the IT system but is facilitated by a Peer Support Team process and the case manager which is specifically tailored for those with chronic disease and disabilities.

In particular, the model uses Action Learning principles which are the underlying process to promote behavior modification and lifestyle change and which places peer support teams at the core of its service delivery model, relying heavily upon the personal relationships, trust factor and emotional support established by peer-to-peer counseling, to IDP compliance and to enhance social service and gainful employment opportunities. The model is a new and unique system of case management using a peer supported, Action Learning approach to empower clients to problem solving their respective service and reimbursement issues with peers and case managers which is a new bottom up approach. The model uses Action Learning to drive a peer support system that empowers clients through customized self management education and problem solving how to self-determine how to improve their health, community integration, employment readiness, financial well being and overall quality of life issues. The model coordinates all system components by a web based platform that broadly shares and integrates information across the full spectrum of service providers, while at the same time honoring matters of privacy and the requirements of a HIPPA compliant data base.

In one embodiment all program modules and stakeholder are unified by an IT platform, coordinating and maintaining connectivity of services and overall communication among all program stakeholders and enabling definitive data capture to validate program premises by measuring and analyzing program indicators/metrics. The IT platform provides the necessary tools and suitable media for customized data collection and capture, analysis, archiving, communication and information sharing among the program stakeholders in a secure compliant IT platform. The IT platform allows for the development of a new and different perspective on outcome development by combining data analysis results from healthcare to community and vocational services allowing for the opportunity to develop new cost/economic models.

In one aspect, the model institutes overall system linkages that are established to encompass local, state and federal systems in assuring seamless delivery, all indexed to a common client centric approach (e.g., Florida DVR and CSAVR at the national level or linkages to Trinidad and Tobago National IT Healthcare System). The model provides a distinctive management architecture, from the standpoint of processes, systems integration and IT. It is a holistic architecture that superintends IT alone. The model provides for active recruitment of eligible clients through the application and implementation of Proactive Intake and Assessment or Stratification processes. The model promotes personal accountability through the development of IDP and self management education, utilizing action learning and peer support team principles to promote self determination, advocacy, gainful employment and independence.

In one arrangement, the model is developed and implemented in phases consisting of primary and secondary intervention strategies. Primary interventions are IDP-based; focusing on the individual beneficiary, while secondary interventions are system-based provisions, including clinical, educational, community, vocational services and benefit counseling. The model can be streamlined for accountability through a mechanism of evaluation for the individual participant and for the system as a whole. The model allows for the development on continuous quality improvement measures through analysis of outcomes. These outcome measures can also develop into policy recommendations. In one aspect, system evaluations focus on both short and long term achievements of predetermined measurable outcomes which can include but are not limited to: Efficacy of recruitment, Attainment of IDP goals (as a joint responsibility of the participant and the system), Clinical goals outcome, Job readiness and actual placements, Assessment of participant satisfaction, and Quality of Life measures.

Where applicable, the present embodiments can be realized in hardware, software or a combination of hardware and software. Any kind of computer system or other apparatus adapted for carrying out the methods described herein are suitable. A typical combination of hardware and software can be a communications device with a computer program that, when being loaded and executed, can control the communications device such that it carries out the methods described herein. Portions of the present method and system may also be embedded in a computer program product, which comprises all the features enabling the implementation of the methods described herein and which when loaded in a computer system, is able to carry out these methods.

While the preferred embodiments of the invention have been illustrated and described, it will be clear that the embodiments of the invention is not so limited. Numerous modifications, changes, variations, substitutions and equivalents will occur to those skilled in the art without departing from the spirit and scope of the present embodiments of the invention as defined by the appended claims.

What is claimed is:

1. A non-transitory computer readable medium having stored thereon a coordinated service delivery program executable by a processor of a computing system, the coordinated service delivery program comprising:
   instructions to stratify, by an intake assessment and recruitment system, a population of clients having chronic disease or disability;
   instructions to recruit, by the intake assessment and recruitment system, the clients that have chronic disease or disability
   instructions to develop, by a primary intervention system, an individual development plan and to enact action-learning through peer support team intervention;
   instructions to provide, by a secondary intervention system, coordination of services; and
   instructions to coordinate services, with an information archive, to monitor and track client progress;
   wherein the coordinated service delivery program is a population-based, client-centric system that combines self-management skills with said services to facilitate functional and psychosocial needs of the client for focusing on community integration and re-employment.

2. The computer readable medium of claim 1, further comprising:
   a program evaluation system for evaluating performance indicators against external indicators from a control group; and
   a policy recommendations system to review findings in view of said performance indicators and to make recommendations based on performance results from said coordinated service delivery program.

3. The computer readable medium of claim 2, wherein the program evaluation system further provides individualized outcomes studies for developing outcome health care studies for evidence-based healthcare programs.

4. The computer readable medium of claim 1, wherein the program evaluation system standardizes said delivery program on clinical, social, behavioral, and economic indicators to measure and analyze overall program and individual client performance.

5. The computer readable medium of claim 1, wherein the intake assessment and recruitment system further comprises collecting long term clinical, behavior, and compliance information to evaluate long term study outcomes; and developing a profile of client qualification criteria for recruiting clients approved with the support of all program stakeholders.

6. The computer readable medium of claim 1, wherein the intake assessment and recruitment system further comprises:
   instructions to enter the analysis of pre-screened clients into a program database;
   instructions to interview the pre-screened clients for directly assessing their needs and interest in participation of said service delivery program;
   instructions to select qualified clients, enrolling clients in an orientation program, and assigning clients to a peer support team;
   instructions to update the program database for qualified and unqualified clients;
   instructions to measure baselines such as clinical history, or quality of life survey; and
   instructions to create an individual development plan (IDP) for a client together with family members, peers, and other program stakeholders of the peer support team.

7. The computer readable medium of claim 1, wherein the intake assessment and recruitment system further comprises instructions to analyze at least one of demographic, employment history, prevalence of chronic disease, other health factors, utilization and other risk stratification factors for chronic disease and disability.

8. The computer readable medium of claim 1, wherein the IDP of the primary services intervention is a multifaceted document which provides the clinical background and life history of the client including at least one of education, training received, family information, and employment history.

9. The computer readable medium of claim 1, wherein the services include:
   a clinical services domain for monitoring chronic disease indicators captured during peer support team meetings that are archived in a database for complying with the IDP;
   an education services domain for providing preventative education for family members of clients with chronic disease and disability;
   a community services domain for supporting active daily living of clients for overcoming employment and community integration barriers; and
   a vocational services domain to facilitate a coordinated continuum of services for providing gainful employment opportunities.

10. The computer readable medium of claim 9, wherein said clinical services domain includes at least one of risk stratification, compliance monitoring, wellness/fitness programs, prescription drug and counseling programs, nutritional and supplemental programs, home healthcare encounters, outpatient primary care encounters, and inpatient encounters.

11. The computer readable medium of claim 1, wherein the program evaluation system further comprises instructions to assess employment indicators including at least one of hours worked, job retention, informed choice, control, satisfaction, level and nature of required supports, and employer satisfaction.

12. A coordinated service delivery system comprising:
   a memory;
   a processor in communication with the memory, the processor operable to execute:
      an intake assessment and recruitment system operable to:
         stratify a population of clients having chronic disease or disability;
         recruit the clients that have chronic disease or disability
      a primary intervention system operable to develop an individual development plan and to enact action-learning through peer support team intervention;
      a secondary intervention system operable to provide coordination of services; and
      an information archive operable to coordinate services, with, to monitor and track client progress;
   wherein the coordinated service delivery system is a population-based, client-centric system that combines self-management skills with said services to facilitate functional and psychosocial needs of the client for focusing on community integration and re-employment.

13. The coordinated service delivery system of claim 12, further comprising:
   a program evaluation system operable to evaluate performance indicators against external indicators from a control group; and
   a policy recommendations system operable to review findings in view of said performance indicators and to make recommendations based on performance results from said coordinated service delivery program.

14. The coordinated service delivery system of claim 13, wherein the program evaluation system is further operable to provide individualized outcomes studies for developing outcome health care studies for evidence-based healthcare programs.

15. The coordinated service delivery system of claim 12, wherein the program evaluation system is further operable to standardize said delivery program on clinical, social, behavioral, and economic indicators to measure and analyze overall program and individual client performance.

16. The coordinated service delivery system of claim 12, wherein the intake assessment and recruitment system further comprises collecting long term clinical, behavior, and compliance information to evaluate long term study outcomes; and developing a profile of client qualification criteria for recruiting clients approved with the support of all program stakeholders.

17. The coordinated service delivery system of claim 12, wherein the intake assessment and recruitment system is further operable to:
   enter the analysis of pre-screened clients into a program database;
   interview the pre-screened clients for directly assessing their needs and interest in participation of said service delivery program;
   select qualified clients, enrolling clients in an orientation program, and assigning clients to a peer support team;
   update the program database for qualified and unqualified clients;

measure baselines such as clinical history, or quality of life survey; and create an individual development plan (IDP) for a client together with family members, peers, and other program stakeholders of the peer support team.

18. The coordinated service delivery system of claim 12, wherein the intake assessment and recruitment system is further operable to analyze at least one of demographic, employment history, prevalence of chronic disease, other health factors, utilization and other risk stratification factors for chronic disease and disability.

19. The coordinated service delivery system of claim 12, wherein the IDP of the primary services intervention is a multifaceted document which provides the clinical background and life history of the client including at least one of education, training received, family information, and employment history.

20. The coordinated service delivery system of claim 12, wherein the services include:

a clinical services domain for monitoring chronic disease indicators captured during peer support team meetings that are archived in a database for complying with the IDP;

an education services domain for providing preventative education for family members of clients with chronic disease and disability;

a community services domain for supporting active daily living of clients for overcoming employment and community integration barriers; and a vocational services domain to facilitate a coordinated continuum of services for providing gainful employment opportunities.

21. The coordinated service delivery system of claim 20, wherein said clinical services domain includes at least one of risk stratification, compliance monitoring, wellness/fitness programs, prescription drug and counseling programs, nutritional and supplemental programs, home healthcare encounters, outpatient primary care encounters, and inpatient encounters.

22. The coordinated service delivery system of claim 12, wherein the program evaluation system is further operable to assess employment indicators including at least one of hours worked, job retention, informed choice, control, satisfaction, level and nature of required supports, and employer satisfaction.

* * * * *